US006689780B1

(12) United States Patent
Beight et al.

(10) Patent No.: US 6,689,780 B1
(45) Date of Patent: Feb. 10, 2004

(54) HETEROROAROMATIC AMIDES AS INHIBITOR OF FACTOR XA

(75) Inventors: Douglas Wade Beight, Frankfort, IN (US); Trelia Joyce Craft, Indianapolis, IN (US); Jeffry Bernard Franciskovich, Zionsville, IN (US); Theodore Goodson, Jr., Indianapolis, IN (US); Steven Edward Hall, Chapel Hill, NC (US); David Kent Herron, Indianapolis, IN (US); Sajan Joseph, Indianapolis, IN (US); Valentine Joseph Klimkowski, Carmel, IN (US); Jeffrey Alan Kyle, Fishers, IN (US); John Joseph Masters, Fishers, IN (US); David Mendel, Indianapolis, IN (US); Guy Milot, Chapel Hill, NC (US); Marta Maria Piñeiro-Nuñez, Brownsburg, IN (US); Jason Scott Sawyer, Indianapolis, IN (US); Robert Theodore Shuman, Sedona, AZ (US); Gerald Floyd Smith, Greenwood, IN (US); Anne Louise Tebbe, Hamburg (DE); Jennifer Marie Tinsley, Ypsilanti, MI (US); Leonard Crayton Weir, Westfield, IN (US); James Howard Wikel, Greenwood, IN (US); Michael Robert Wiley, Indianapolis, IN (US); Ying Kwong Yee, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/857,749
(22) PCT Filed: Dec. 15, 1999
(86) PCT No.: PCT/US99/29887
§ 371 (c)(1),
(2), (4) Date: Jun. 8, 2001

(87) PCT Pub. No.: WO00/39117
PCT Pub. Date: Jul. 6, 2000

Related U.S. Application Data

(60) Provisional application No. 60/113,452, filed on Dec. 23, 1998.

(51) Int. Cl.[7] .................. C07D 401/14; C07D 213/82; C07D 417/14; A61K 31/4545; A61P 7/02
(52) U.S. Cl. .................. 514/252.03; 546/193; 514/318; 514/275; 514/255.05; 514/255.06; 544/238; 544/331; 544/405
(58) Field of Search .......................... 546/193; 514/318, 514/252.03, 275, 255.05, 255.06; 544/238, 331, 405

(56) References Cited

U.S. PATENT DOCUMENTS

| 5,576,343 | A | 11/1996 | Nagahara et al. | ............ 514/422 |
|---|---|---|---|---|
| 6,140,351 | A | 10/2000 | Arnaiz et al. | ................ 514/336 |
| 6,380,221 | B1 | 4/2002 | Arnaiz et al. | ................ 514/337 |

FOREIGN PATENT DOCUMENTS

| WO | WO 99/00121 | 1/1999 |
|---|---|---|
| WO | WO 99/00126 | 1/1999 |
| WO | WO 99/00127 | 1/1999 |
| WO | WO 99/00128 | 1/1999 |
| WO | WO 99/32477 | 7/1999 |
| WO | WO 00/39092 | 7/2000 |
| WO | WO 00/39111 | 7/2000 |
| WO | WO 00/39118 | 7/2000 |

*Primary Examiner*—Mukund J. Shah
*Assistant Examiner*—Hong Liu
(74) *Attorney, Agent, or Firm*—Thomas E. Jackson

(57) ABSTRACT

This application relates to heteroaromatic amides (or a pharmaceutically acceptable salt thereof) as defined herein, pharmaceutical compositions thereof, and its use as an inhibitor of factor Xa, as well as a process for its preparation and intermediates therefor.

13 Claims, No Drawings

HETEROROAROMATIC AMIDES AS INHIBITOR OF FACTOR XA

This application claims the benefit of U.S. Provisional Application No. 60/113,452, filed Dec. 23, 1998.

This invention relates to antithrombotic heteroaromatic amides which demonstrate activity as inhibitors of factor Xa and, accordingly, which are useful anticoagulants in mammals. In particular it relates to heteroaromatic amides having high anticoagulant activity, and antithrombotic activity. Thus, this invention relates to new amides which are inhibitors of factor Xa, pharmaceutical compositions containing the amides as active ingredients, and the use of the amides as anticoagulants for prophylaxis and treatment of thromboembolic disorders such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process. In addition, the heteroaromatic amides are useful as anticoagulants in in vitro applications.

The process of blood coagulation, thrombosis, is triggered by a complex proteolytic cascade leading to the formation of thrombin. Thrombin proteolytically removes activation peptides from the Aα-chains and the Bβ-chains of fibrinogen, which is soluble in blood plasma, initiating insoluble fibrin formation. The formation of thrombin from prothrombin is catalyzed by factor Xa.

Anticoagulation currently is achieved by the administration of heparins and coumarins. Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because clot-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin time (APTT) assay). Coumarins impede the generation of thrombin by blocking the posttranslational gamma-carboxylation in the synthesis of prothrombin and other proteins of this type. Because of their mechanism of action, the effect of coumarins can only develop slowly, 6–24 hours after administration. Further, they are not selective anticoagulants. Coumarins also require monitoring with coagulation assays (particularly the prothrombin time (PT) assay).

Recently, interest has grown in small synthetic molecules which demonstrate potent direct inhibition of thrombin and factor Xa. See, Joseph P. Vacca (Annette M. Doherty Section Editor), *Annual Reports in Medicinal Chemistry*, (1998), 33, 81–90.

Although the heparins and coumarins are effective anticoagulants, there still exists a need for anticoagulants which act selectively on factor Xa or thrombin, and which, independent of antithrombin III, exert inhibitory action shortly after administration, preferably by an oral route, and do not interfere with lysis of blood clots, as required to maintain hemostasis.

The present invention is directed to the discovery that the amides of the present invention, as defined below, are potent inhibitors of factor Xa which may have high bioavailability following oral administration.

According to the invention there is provided a compound of formula I

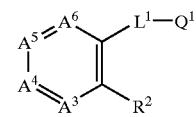

I (or a pharmaceutically acceptable salt thereof) wherein:

$A^3$, $A^4$, $A^5$ and $A^6$, together with the two carbons to which they are attached, complete a substituted heteroaromatic ring in which
  (a) one of $A^3$, $A^4$, $A^5$ and $A^6$ is N, and each of the others is $CR^3$, $CR^4$, $CR^5$ or $CR^6$, respectively; or
  (b) two non-adjacent residues of $A^3$, $A^4$, $A^5$ and $A^6$ are each N, and each of the others is $CR^3$, $CR^4$, $CR^5$ or $CR^6$, respectively; wherein
    each of $R^3$, $R^4$, $R^5$ and $R^6$ is independently hydrogen or methyl, or one of $R^3$, $R^4$, $R^5$ and $R^6$ attached to a carbon which is not bonded to an N-atom is chloro and the others are hydrogen;

$L^1$ is —CO—NH— such that —$L^1$—$Q^1$ is —CO—NH—$Q^1$;

$Q^1$ is 2-pyridinyl (which bears a methyl, methoxy, methylthio, fluoro or chloro substituent at the 5-position), 3-pyridinyl (which bears a methyl, fluoro or chloro substituent at the 6-position), 2-pyrimidinyl (which may bear a methyl, fluoro or chloro substituent at the 5-position), 3-pyridazinyl (which may bear a methyl, fluoro or chloro substituent at the 6-position) or 2-benzothiazolyl (which may bear a methyl, fluoro, chloro or bromo substituent at the 6-position);

$R^2$ is —$L^2$—$Q^2$ in which —$L^2$— is —NH—CO—, —NH—CO—X—, —NH—CO—O—X—, —NH—CO—NH—X— or —NH—CH$_2$—; and $Q^2$ is $Q^{2A}$, $Q^{2B}$, $Q^{2C}$, $Q^{2D}$, $Q^{2E}$ or $Q^{2F}$ wherein X is a single bond or methylene and the values of $L^2$ and $Q^2$ are together selected from —NH—CO—X—$Q^{2A}$, —NH—CO—O—X—$Q^{2A}$, —NH—CO—NH—X—$Q^{2A}$, —NH—CH$_2$—$Q^{2A}$, —NH—CO—X—$Q^{2B}$, —NH—CO—$Q^{2C}$, —NH—CO—$Q^{2D}$, —NH—CO—$Q^{2E}$ and —NH—CO—$Q^{2F}$ in which:

$Q^{2A}$ (showing the $L^2$ to which it is attached) is

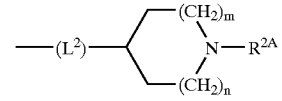

in which
  each of m and n independently is 0 or 1, and
  $R^{2A}$ is hydrogen, t-butyl, methylsulfonyl, —CHR$^y$R$^z$, —CHR$^w$R$^x$, or 4-pyridinyl (which is unsubstituted or bears a substituent R$^v$ at the 2- or 3-position) wherein R$^v$ is methyl, hydroxymethyl, {(1–2C)alkoxy}carbonyl; cyano, carbamoyl, thiocarbamoyl, or N-hydroxyamidino;
  each of R$^w$ and R$^x$ independently is hydrogen or (1–3C)normal alkyl; or —CHR$^w$R$^x$ is 2-indanyl or (showing the nitrogen to which it is attached) is

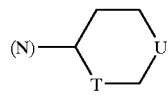

in which T is a single bond or methylene and U is methylene, ethylene, oxy, —S(O)$_q$— (wherein q is 0, 1 or 2) or imino (which may bear a methyl substituent), or T is ethan-1,1-diyl and U is a single bond or methylene;

$R^y$ is hydrogen or methyl; and $R^z$ is isopropyl, t-butyl, (3–6C)cycloalkyl, phenyl (which is unsubstituted or bears one or more substituents independently selected from halo, methyl, methoxy and hydroxy), 4-quinolinyl or heteroaryl (which heteroaryl is a 5-membered aromatic ring which includes one to four heteroatoms selected from sulfur, oxygen and nitrogen or is a 6-membered aromatic ring which includes one to three nitrogen atoms, wherein the heteroaryl is attached at carbon and may bear one or more methyl substituents on carbon or nitrogen);

$Q^{2B}$ is 1-piperazinyl which bears at the 4-position the group $R^{2A}$ (defined as above);

$Q^{2C}$ is 3,4-didehydropiperidin-4-yl which bears at the 1-position the group $R^{2A}$ (defined as above);

$Q^{2D}$ is cyclohexyl which bears at the 4-position the group —NR$^s$R$^t$ in which each of $R^s$ and $R^t$ independently is hydrogen or methyl or $R^s$ and $R^t$ together are trimethylene or tetramethylene;

$Q^{2E}$ is 1-piperidinyl which bears at the 4-position the group —NR$^s$R$^t$ (defined as above); and $Q^{2F}$ (showing the $L^2$ to which it is attached) is

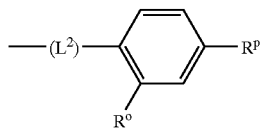

in which $R^o$ is hydrogen, halo, (1–6C)alkyl, hydroxy, (1–4C)alkoxy, benzyloxy or (1–4C)alkylthio; and $R^p$ is 1-hydroxyethyl, 1-hydroxy-1-methylethyl, 1-methoxy-1-methylethyl, 4-piperidinyl, 4-pyridinyl, dimethylaminosulfonyl or —J—R$^q$ in which J is a single bond, methylene, carbonyl, oxy, —S(O)$_q$— (wherein q is 0, 1 or 2), or —NR$^r$— (wherein R$^r$ is hydrogen or methyl); and R$^q$ is (1–6C)alkyl, phenyl, 3-pyridyl or 4-pyridyl.

As used herein, the expression a compound of formula I or the expression a compound of the invention includes the compound and any conventional prodrug thereof, as well as a pharmaceutically acceptable salt of said compound or prodrug.

A pharmaceutically acceptable salt of an antithrombotic agent of the instant invention includes one which is an acid-addition salt made from a basic compound of formula I and an acid which provides a pharmaceutically acceptable anion, as well as a salt which is made from an acidic compound of formula I and a base which provides a pharmaceutically acceptable cation. Thus, a salt of a novel compound of formula I as provided herein made with an acid or base which affords a pharmaceutically acceptable counterion provides a particular aspect of the invention. Examples of such acids and bases are provided hereinbelow.

As an additional aspect of the invention there is provided a pharmaceutical formulation comprising in association with a pharmaceutically acceptable carrier, diluent or excipient, a novel compound of formula I (or a pharmaceutically acceptable salt thereof) as provided in any of the descriptions herein.

In addition, there is provided the use of a factor Xa inhibiting compound of formula I (or prodrug or salt) as described herein as an active ingredient in the manufacture of a medicament for use in producing an anticoagulant or antithrombotic effect.

The present invention also provides a method of inhibiting coagulation in a mammal comprising administering to a mammal in need of treatment, a coagulation inhibiting dose of a factor Xa inhibiting compound of formula I having any of the definitions herein.

The present invention further provides a method of inhibiting factor Xa comprising administering to a mammal in need of treatment, a factor Xa inhibiting dose of a factor Xa inhibiting compound of formula I having any of the definitions herein.

Further, the present invention provides a method of treating a thromboembolic disorder comprising administering to a mammal in need of treatment, an effective dose of a factor Xa inhibiting compound of formula I having any of the definitions herein.

In addition, there is provided the use of a factor Xa inhibiting compound of formula I having any of the definitions herein for the manufacture of a medicament for treatment of a thromboembolic disorder.

As an additional feature of the invention there is provided a pharmaceutical formulation comprising in association with a pharmaceutically acceptable carrier, diluent or excipient, a prodrug of a factor Xa inhibiting compound of formula I (or of a pharmaceutically acceptable salt thereof) as provided in any of the descriptions herein.

In this specification, the following definitions are used, unless otherwise described: Halo is fluoro, chloro, bromo or iodo. Alkyl, alkoxy, etc. denote both straight and branched groups; but reference to an individual radical such as "propyl" embraces only the straight chain ("normal") radical, a branched chain isomer such as "isopropyl" being specifically denoted.

Particular values are listed below for radicals, substituents, and ranges, for illustration only, and they do not exclude other defined values or other values within defined ranges for the radicals and substituents.

For an alkyl group or the alkyl portion of an alkyl containing group such as, for example alkoxy, a particular value for (1–2C)alkyl is methyl or ethyl, and more particularly is methyl; for (1–3C)normal alkyl is methyl, ethyl or propyl; for (1–4C)alkyl is methyl, ethyl, propyl, isopropyl, butyl, isobutyl, or t-butyl, and more particularly is methyl, isopropyl, butyl or t-butyl; for (1–6C)alkyl is methyl, ethyl, propyl, butyl, pentyl or hexyl, and more particularly is methyl, butyl, or hexyl. A particular value for (3–6C) cycloalkyl is cyclopropyl, cyclobutyl, cyclopenytyl or cyclohexyl. A particular value for halo is bromo or chloro, and more particularly is chloro.

A particular value for $Q^1$ is 5-chloropyridin-2-yl or 6-chloropyridazin-3-yl. A particular value for $R^2$ is (1-isopropylpiperidin-4-ylcarbonyl)amino, (1-cyclohexylpiperidin-4-ylcarbonyl)amino, [1-(tetrahydropyran-4-yl)-piperidin-4-ylcarbonyl]amino, or [1-(4-pyridinyl)piperidin-4-ylmethyl]amino. A particular set of values for $A^3$—$A^6$ is that $A^3$ is N and each of $A^4$—$A^6$ is $CR^4$—$CR^6$ in which each of $R^4$—$R^6$ is hydrogen or $R^4$ and $R^6$ are each hydrogen and $R^5$ is chloro. Another set of values for $A^3$—$A^6$ is that $A^6$ is N and each of $A^3$—$A^5$ is $CR^3$—$CR^5$ in which each of $R^3$—$R^5$ is hydrogen or $R^3$ and $R^4$ are each hydrogen and $R^5$ is methyl.

A particular species is one those listed below as example 6, 8, 14, 15 or 17.

It will be appreciated that certain compounds of formula I (or salts or prodrugs, etc.) may exist in, and be isolated in, isomeric forms, including tautomeric forms, cis- or trans-isomers, as well as optically active, racemic, or diastereomeric forms. It is to be understood that the present invention encompasses a compound of formula I in any of the tautomeric forms or as an a mixture thereof; or as a mixture of diastereomers, as well as in the form of an individual diastereomer, and that the present invention encompasses a compound of formula I as a mixture of enantiomers, as well as in the form of an individual enantiomer, any of which mixtures or form possesses inhibitory properties against factor Xa, it being well known in the art how to prepare or isolate particular forms and how to determine inhibitory properties against factor Xa by standard tests including those described below.

In addition, a compound of formula I (or salt or prodrug, etc.) may exhibit polymorphism or may form a solvate with water or an organic solvent. The. present invention also encompasses any such polymorphic form, any solvate or any mixture thereof.

A prodrug of a compound of formula I may be one formed in a conventional manner with a functional group of the compound, such as with an amino, hydroxy or carboxy group.

A compound of formula I may be prepared by processes which include processes known in the chemical art for the production of structurally analogous compounds or by a novel process described herein. A process for the preparation of a compound of formula I (or a pharmaceutically acceptable salt thereof) and novel intermediates for the manufacture of a compound of formula I as defined above provide further features of the invention and are illustrated by the following procedures in which the meanings of the generic radicals are as defined above, unless otherwise specified. It will be recognized that it may be preferred or necessary to prepare a compound of formula I in which a functional group is protected using a conventional protecting group, then to remove the protecting group to provide the compound of formula I.

Thus, there is provided a process for preparing a compound of formula I (or a pharmaceutically acceptable salt thereof) as provided in any of the above descriptions which is selected from any of those described in the examples, including the following.

(A) For a compound of formula I in which —L²—Q², is —NH—CO—Q², —NH—CO—X—Q², —NH—CO—O—X—Q² or —NH—CO—NH—X—Q², acylating an amine of formula II,

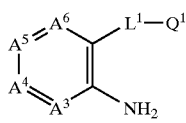

II using a corresponding acid of formula HO—CO—Q², HO—CO—X—Q², HO—CO—O—X—Q², or HO—CO—NH—X—Q², or an activated derivative thereof. Typical activated derivatives include the acid halides, activated esters, including 4-nitrophenyl esters and those derived from coupling reagents, as well as (when the product is a urea) isocyanates. Typical procedures include those described at example 2-B, example 3-B and example 9-A.

(B) For a compound of formula I in which —L²—Q² is —NH—CH₂—Q², and (preferably) at least one of A³ and A⁵ is N, substituting the group Yᵃ of a compound of formula III

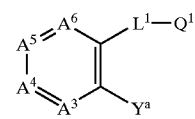

III in which Yᵃ is a conventional leaving group for nucleophilic aromatic substitution with an amine of formula NH₂—CH₂—Q². As used herein, a leaving group "Yᵃ" is a moiety which is displaced in an aromatic (or heteroaromatic) nucleophilic substitution reaction, for example a halo group (such as fluoro or chloro), an alkoxy group (such as methoxy), a sulfonate ester group (such as methylsulfonyloxy, p-toluyl-sulfonyloxy or trifluoromethylsulfonyloxy), or the reactive species derived from treating an alcohol with triphenylphospine, diethyl azodicarboxylate and triethyl amine (in a Mitsunobu reaction). The substitution may be carried out by heating a mixture of the reagents in a polar solvent, for example in ethanol in a sealed tube as described at example 14-B or in refluxing pyridine as described at example 23-B.

(C) Acylating an amine of formula H₂N—Q¹, or a deprotonated derivative thereof, using an acid of formula IV, or an activated derivative thereof.

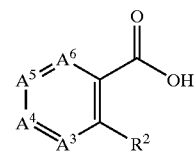

IV

Typical deprotonated derivatives of the amine H₂N—Q¹ include, for example, that derived from treatment of the amine with an organomagnesium reagent, for example, with allylmagnesium bromide or methylmagnesium bromide. Typical activated derivatives include the acid halides, activated esters, including 4-nitrophenyl esters and those derived from coupling reagents. A typical procedure is for example one using an acid chloride as described in example 4.

For a compound of formula I in which R² is of the form —NH—CO—Q², the activated acid may be a [1,3]oxazine of formula IVa,

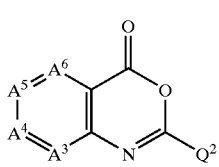

IVa wherein Q² represents, for example, Q²ᴬ, Q²ᴮ, Q²ᶜ, Q²ᴰ, Q²ᴱ or Q²ᶠ. A typical pro cedure is one such as described at example 21-H.

For a compound of formula I in which R² is of the form —NH—CH₂—Q², the activated acid may be an anhydride of formula IVb,

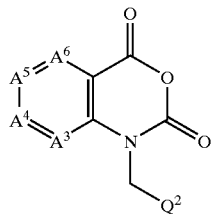

IVb wherein $Q^2$ represents $Q^{2A}$. A typical procedure is that described at example 1-C.

(D) For a compound of formula I in which $R^2$ is —NH—$CH_2$—$Q^{2A}$, alkylating an amine of formula II directly, using a compound of formula Y—$CH_2$—$Q^{2A}$, or (preferably) indirectly by reductive alkylation using an aldehyde of formula $Q^{2A}$—CHO. In the reductive alkylation the intermediate imine of formula V or acid addition salt thereof (which provide a further aspect of the invention),

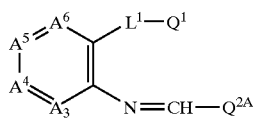

V may be formed in situ and reduced directly, or may be isolated prior to reduction, for example as described at example 13-D where the reduction is carried out using borane trimethylamine complex in glacial acetic acid.

(E) For a compound of formula I in which $R^2$ is —NH—CO—O—X—$Q^{2A}$, or —NH—CO—NH—X—$Q^{2A}$, acylating an alcohol of formula HO—X—$Q^{2A}$ or an amine of formula $NH_2$—X—$Q^{2A}$, using an activated derivative of an acid of formula VI,

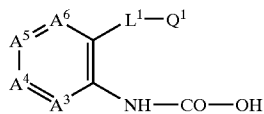

VI particularly, the corresponding isocyanate or 4-nitrophenyl ester.

(F) For a compound of formula I in which $R^2$ is —NH—C—X—$Q^{2B}$ in which X is a single bond, acylating at the 1-position a piperazine of formula H—$Q^{2B}$, using an activated derivative of an acid of formula VI, particularly, the corresponding isocyanace or 4-nitrophenyl ester.

(G) For a compound of formula I in which $R^2$ is —NH—CO—X—$Q^{2B}$ in which X is methylene, alkylating at the 1-position a piperazine of formula H—$Q^{2B}$, using an alkylating agent of formula VII

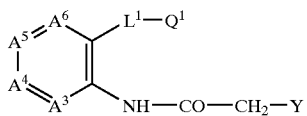

VII in which Y is a leaving group.

(H) For a compound of formula I in which $R^{2A}$ is methylsulfonyl, substituting the amino nitrogen of a corresponding compound of formula I in which $R^{2A}$ is hydrogen using an activated derivative of methanesulfonic acid, for example using methanesulfonyl chloride in the presence of added base.

(I) For a compound of formula I in which $R^{2A}$ is —$CHR^yR^z$ or —$CHR^wR^x$, alkylating the amino nitrogen of a corresponding compound of formula I in which $R^{2A}$ is hydrogen using an alkylating agent of formula Y—$CHR^yR^z$ or Y—$CHR^wR^x$ or, preferably, reductively alkylating the amine using a compound of formula $R^y$—CO—$R^z$ or $R^w$—CO—$R^x$. The direct alkylation may be completed in a polar solvent in the presence of a base. The reductive alkylation conveniently is carried out, for example, using sodium cyanoborohydride in methanol/acetic acid as described at example 13-E or using sodium triacetoxyborohydride in an inert solvent such as 1,2-dichloroethane along with an excess of the carbonyl compound and glacial acetic acid as described at example 6-C.

(J) For a compound of formula I in which $R^{2A}$ is 4-pyridinyl (which is unsubstituted or bears a substituent $R^v$ at the 2- or 3-position), substituting the amino nitrogen of a corresponding compound of formula I in which $R^{2A}$ is hydrogen using a corresponding pyridine reagent bearing a leaving group Y at the 4-position, for example with a 4-chloropyridine in ethanol as described at example 18.

(K) For a compound of formula I in which $R^{2A}$ is 4-pyridinyl in which $R^v$ is alkoxycarbonyl, esterifying a corresponding compound of formula I in which $R^v$ is carboxy.

(L) For a compound of formula I in which $R^{2A}$ is 4-pyridinyl in which $R^v$ is hydroxymethyl, reducing the ester of a corresponding compound of formula I in which $R^v$ is alkoxycarbonyl.

(M) For a compound of formula I in which $R^{2A}$ is 4-pyridinyl in which $R^v$ is carbamoyl, amidating the ester of a corresponding compound of formula I in which $R^v$ is alkoxycarbonyl.

(N) For a compound of formula I in which $R^{2A}$ is 4-pyridinyl in which $R^v$ is thiocarbamoyl, adding $H_2S$ to the nitrile of a corresponding compound of formula I in which $R^v$ is cyano.

(O) For a compound of formula I in which $R^{2A}$ is 4-pyridinyl in which $R^v$ is N-hydroxyamidino, adding $H_2NOH$ to the nitrile of a corresponding compound of formula I in which $R^v$ is cyano. The addition may be direct or indirect, such as via an imidate ester or by treating a compound in which $R^v$ is thiocarbamoyl with methyl iodide to form a thioimidate ester, then treatment with hydroxylamine.

(P) For a compound of formula I in which $R^{2A}$ is 4-pyridinyl in which $R^v$ is carboxy, decomposing the ester of a corresponding compound of formula I in which $R^v$ is alkoxycarbonyl.

(Q) For a compound of formula I in which —$NR^sR^t$ is other than amino, alkylating a corresponding compound of formula I in which —$NR^sR^t$ is amino using a conventional method. When $R^s$ and $R^t$ together are trimethylene or tetramethylene, a difunctional alkylating agent, such as 1,3-dibromopropane or 1,4-dibromobutane is preferred.

(R) For a compound of formula I which bears —$NR^sR^t$, reductively alkylating H—$NR^sR^t$ using a corresponding compound but in which the carbon to bear the —$NR^sR^t$ group bears an oxo group, for example, using a procedure similar to one of procedure (I) above.

(S) For a compound of formula I in which $R^p$ is 1-hydroxy-1-methylethyl, adding a methyl group to the carbonyl group of a corresponding compound of formula I in which $R^p$ is acetyl using an organometallic reagent such as, for example, methylmagnesium bromide.

(T) For a compound of formula I in which $R^p$ is 1-methoxy-1-methylethyl, treating a corresponding compound of formula I in which R$^p$ is 1-hydroxy-1-methylethyl with methanol and an acid catalyst.

Whereafter, for any of the above procedures, when a functional group is protected using a protecting group, removing the protecting group.

Whereafter, for any of the above procedures, when a pharmaceutically acceptable salt of a compound of formula I is required, it is obtained by reacting the basic form of a basic compound of formula I with an acid affording a physiologically acceptable counterion or the acidic form of an acidic compound of formula I with a base affording a physiologically acceptable counterion or by any other conventional procedure.

A novel intermediate or starting material compound such as, for example, a novel compound of formula II, III, IV or VI, etc., provides a further aspect of the invention. The various starting materials may be made by processes which include processes known in the chemical art for the production of structurally analogous compounds or by a novel process described herein or one analogous thereto.

As mentioned above, a compound corresponding to a compound of formula I but in which a functional group is protected may serve as an intermediate for a compound of formula I. Accordingly, such a protected intermediate for a novel compound of formula I provides a further aspect of the invention. Thus, as one particular aspect of the invention, there is provided a compound corresponding to a novel compound of formula I as defined above in which R$^4$ is hydroxy, but in which the corresponding substituent is —OP$^p$ in place of hydroxy, wherein P$^p$ is a phenol protecting group other than (1–4C)alkyl or benzyl. Phenol protecting groups are well known in the art, for example as described in T. W. Greene and P. G. M. Wuts, "Protecting Groups in Organic Synthesis" (1991). Further, P$^p$ may denote a functionalized resin, for example as disclosed in H. V. Meyers, et al., *Molecular Diversity*, (1995), 1, 13–20.

As mentioned above, the invention includes a pharmaceutically acceptable salt of the factor Xa inhibiting compound defined by the above formula I. A basic compound of this invention possesses one or more functional groups sufficiently basic to react with any of a number of inorganic and organic acids affording a physiologically acceptable counterion to form a pharmaceutically acceptable salt. Acids commonly employed to form pharmaceutically acceptable acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromobenzenesulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts include those formed with mineral acids such as hydrochloric acid, hydrobromic acid and sulfuric acid.

For a compound of formula I which bears an acidic moiety, such as a carboxy group, a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as triethylamine, morpholine, piperidine and triethanolamine.

If not commercially available, a necessary starting material for the preparation of a compound of formula I may be prepared by a procedure which is selected from standard techniques of organic chemistry, including aromatic and heteroaromatic substitution and transformation, from techniques which are analogous to the syntheses of known, structurally similar compounds, and techniques which are analogous to the above described procedures or procedures described in the Examples. It will be clear to one skilled in the art that a variety of sequences is available for the preparation of the starting materials. Starting materials which are novel provide another aspect of the invention.

Selective methods of substitution, protection and deprotection are well known in the art for preparation of a compound such as one of formula II, III, IV or VI discussed above.

Generally, a basic compound of the invention is isolated best in the form of an acid addition salt. A salt of a compound of formula I formed with an acid such as one of those mentioned above is useful as a pharmaceutically acceptable salt for administration of the antithrombotic agent and for preparation of a formulation of the agent. Other acid addition salts may be prepared and used in the isolation and purification of the compounds.

As noted above, the optically active isomers and diastereomers of the compounds of formula I are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors. Further details regarding resolutions can be obtained in Jacques, et al., *Enantiomers, Racemates, and Resolutions*, John Wiley & Sons, 1981.

The compounds of the invention are believed to selectively inhibit factor Xa over other proteinases and nonenzyme proteins involved in blood coagulation without appreciable interference with the body's natural clot lysing ability (the compounds have a low inhibitory effect on fibrinolysis). Further, such selectivity is believed to permit use with thrombolytic agents without substantial interference with thrombolysis and fibrinolysis.

The invention in one of its aspects provides a method of inhibiting factor Xa in mammals comprising administering to a mammal in need of treatment an effective (factor Xa inhibiting) dose of a compound of formula I.

In another of its aspects, the invention provides a method of treating a thromboembolic disorder comprising administering to a mammal in need of treatment an effective (thromboembolic disorder therapeutic and/or prophylactic amount) dose of a compound of formula I.

The invention in another of its aspects provides a method of inhibiting coagulation in a mammal comprising administering to a mammal in need of treatment an effective (coagulation inhibiting) dose of a compound of formula I.

The factor Xa inhibition, coagulation inhibition and thromboembolic disorder treatment contemplated by the present method includes both medical therapeutic and/or prophylactic treatment as appropriate.

In a further embodiment, the invention relates to treatment, in a human or animal, of a condition where inhibition of factor Xa is required. The compounds of the invention are expected to be useful in mammals, including man, in treatment or prophylaxis of thrombosis and hypercoagulability in blood and tissues. Disorders in which the compounds have a potential utility are in treatment or prophylaxis of thrombosis and hypercoagulability in blood and tissues. Disorders in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in the treatment or prophylaxis of atherosclerotic disorders (diseases) such as coronary arterial disease, cerebral arterial disease and peripheral arterial disease. Further, the compounds are expected to be useful together with thrombolytics in myocardial infarction. Further, the compounds have expected utility in prophylaxis for reocclusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs, including joint replacement, and cardiac valves. Further, the compounds have expected utility in anticoagulant treatment in hemodialysis and disseminated intravascular coagulation. A further expected utility is in rinsing of catheters and mechanical devices used in patients in vivo, and as an anticoagulant for preservation of blood, plasma and other blood products in vitro. Still further, the compounds have expected utility in other diseases where blood coagulation could be a fundamental contributing process or a source of secondary pathology, such as cancer, including metastasis, inflammatory diseases, including arthritis, and diabetes. The anticoagulant compound is administered orally or parenterally, e.g. by intravenous infusion (iv), intramuscular injection (im) or subcutaneously (sc).

The specific dose of a compound administered according to this invention to obtain therapeutic and/or prophylactic effects will, of course, be determined by the particular circumstances surrounding the case, including, for example, the compound administered, the rate of administration, the route of administration, and the condition being treated.

A typical daily dose for each of the above utilities is between about 0.01 mg/kg and about 1000 mg/kg. The dose regimen may vary e.g. for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent e.g. tissue plasminogen activator (t-PA), modified t-PA, streptokinase or urokinase. In cases when clot formation has occurred and an artery or vein is blocked, either partially or totally, a clot lysing agent is usually employed. A compound of the invention can be administered prior to or along with the lysing agent or subsequent to its use, and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the occurrence or reoccurrence of clot formation.

The method of this invention is also practiced in conjunction with aspirin. A compound of the invention can be administered prior to or along with aspirin or subsequent to its use to prevent the occurrence or reoccurrence of clot formation. As stated above, preferably a compound of the present invention is administered in conjunction with a clot lysing agent and aspirin.

This invention also provides a pharmaceutical composition for use in the above described therapeutic method. A pharmaceutical composition of the invention comprises an effective factor Xa inhibiting amount of a compound of formula I in association with a pharmaceutically acceptable carrier, excipient or diluent.

The active ingredient in such formulations comprises from 0.1 percent to 99.9 percent by weight of the formulation. By "pharmaceutically acceptable" it is meant the carrier, diluent or excipient must be compatible with the other ingredients of the formulation and not deleterious to the recipient thereof.

For oral administration the antithrombotic compound is formulated in gelatin capsules or tablets which may contain excipients such as binders, lubricants, disintegration agents and the like. For parenteral administration the antithrombotic is formulated in a pharmaceutically acceptable diluent e.g. physiological saline (0.9 percent), 5 percent dextrose, Ringer's solution and the like.

The compound of the present invention can be formulated in unit dosage formulations comprising a dose between about 0.1 mg and about 1000 mg. Preferably the compound is in the form of a pharmaceutically acceptable salt such as for example the sulfate salt, acetate salt or a phosphate salt. An example of a unit dosage formulation comprises 5 mg of a compound of the present invention as a pharmaceutically acceptable salt in a 10 mL sterile glass ampoule. Another example of a unit dosage formulation comprises about 10 mg of a compound of the present invention as a pharmaceutically acceptable salt in 20 mL of isotonic saline contained in a sterile ampoule.

The compounds can be administered by a variety of routes including oral, rectal, transdermal, subcutaneous, intravenous, intramuscular, and intranasal. The compounds of the present invention are preferably formulated prior to administration.

The present pharmaceutical compositions are prepared by known procedures using well known and readily available ingredients. The compositions of this invention may be formulated so as to provide quick, sustained, or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like.

The following formulation examples are illustrative only and are not intended to limit the scope of the invention in any way. "Active ingredient," of course, means a compound according to formula I or a pharmaceutically acceptable salt or solvate thereof.

Formulation 1: Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2: A tablet is prepared using the ingredients below:

|  | Quantity (mg/tablet) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3: An aerosol solution is prepared containing the following components:

|  | Weight |
| --- | --- |
| Active ingredient | 0.25 |
| Ethanol | 29.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4: Tablets, each containing 60 mg of active ingredient, are made as follows:

| Active ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5: Capsules, each containing 80 mg of active ingredient, are made as follows:

| Active ingredient | 80 mg |
| --- | --- |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6: Suppositories, each containing 225 mg of active ingredient, are made as follows:

| Active ingredient | 225 mg |
| --- | --- |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7: Suspensions, each containing 50 mg of active ingredient per 5 mL dose, are made as follows:

| Active ingredient | 50 mg |
| --- | --- |
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8: An intravenous formulation may be prepared as follows:

| Active ingredient | 100 mg |
| --- | --- |
| Isotonic saline | 1,000 mL |

The solution of the above ingredients generally is administered intravenously to a subject at a rate of 1 mL per minute.

The ability of a compound of the present invention to be an effective and orally active factor Xa inhibitor may be evaluated in one or more of the following assays or in other standard assays known to those in the art.

The inhibition by a compound of the inhibition of a serine protease of the human blood coagulation system or of the fibrinolytic system, as well as of trypsin, is determined in vitro for the particular enzyme by measuring its inhibitor binding affinity in an assay in which the enzyme hydrolyzes a particular chromogenic substrate, for example as described in Smith, G. F.; Gifford-Moore, D.; Craft, T. J.; Chirgadze, N.; Ruterbories, K. J.; Lindstrom, T. D.; Satterwhite, J. H. Efegatran: A New Cardiovascular Anticoagulant. *New Anticoagulants for the Cardiovascular Patient*; Pifarre, R., Ed.; Hanley & Belfus, Inc.: Philadelphia, 1997; pp. 265–300. The inhibitor binding affinity is measured as apparent association constant Kass which is the hypothetical equilibrium constant for the reaction between enzyme and the test inhibitor compound (I).

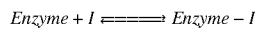

$$Kass = \frac{[Enzyme - I]}{[(Enzyme) \times (I)]}$$

Conveniently, enzyme inhibition kinetics are performed in 96-well polystyrene plates and reaction rates are determined from the rate of hydrolysis of appropriate p-nitroanilide substrates at 405 nm using a Thermomax plate reader from Molecular Devices (San Francisco, Calif.). The same protocol is followed for all enzymes studied: 50 μL buffer (0.03 M Tris, 0.15 M NaCl pH 7) in each well, followed by 25 μL of inhibitor solution (in 100% methanol, or in 50% v:v aqueous methanol) and 25 μL enzyme solution; within two minutes, 150 μL aqueous solution of chromogenic substrate (0.25 mg/mL) is added to start the enzymatic reaction. The rates of chromogenic substrate hydrolysis reactions provide a linear relationship with the enzymes studied such that free enzyme can be quantitated in reaction mixtures. Data is analyzed directly as rates by the Softmax program to produce [free enzyme] calculations for tight-binding Kass determinations. For apparent Kass determinations, 1.34 nM human factor Xa is used to hydrolyze 0.18 mM BzIle-Glu-Gly-Arg-pNA; 5.9 nM human thrombin or 1.4 nM bovine trypsin is used to hydrolyze 0.2 mM BzPhe-Val-Arg-pNA; 3.4 nM human plasmin is used with 0.5 mM HD-Val-Leu-Lys-pNA; 1.2 nM human nt-PA is used with 0.81 mM HD-Ile-Pro-Arg-pNA; and 0.37 nM urokinase is used with 0.30 mM pyro-gfsGlu-Gly-Arg-pNA.

Kass is calculated for a range of concentrations of test compounds and the mean value reported in units of liter per mole. In general, a factor Xa inhibiting compound of formula I of the instant invention, as exemplified herein, exhibits a Kass of 0.1 to $0.5 \times 10^6$ L/mole or much greater.

The factor Xa inhibitor preferably should spare fibrinolysis induced by urokinase, tissue plasminogen activator (t-PA) and streptokinase. This would be important to the therapeutic use of such an agent as an adjunct to streptokinase, tp-PA or urokinase thrombolytic therapy and to the use of such an agent as an endogenous fibrinolysis-sparing (with respect to t-PA and urokinase) antithrombotic agent. In addition to the lack of interference with the amidase activity of the fibrinolytic proteases, such fibrinolytic system sparing can be studied by the use of human plasma clots and their lysis by the respective fibrinolytic plasminogen activators.

Materials

Dog plasma is obtained from conscious mixed-breed hounds (either sex Butler Farms, Clyde, N.Y., U.S.A.) by venipuncture into 3.8 percent citrate. Fibrinogen is prepared from fresh dog plasma and human fibrinogen is prepared from in-date ACD human blood at the fraction I-2 according to previous procedures and specification. Smith, *Biochem. J.*, 185, 1–11 (1980; and Smith, et al., *Biochemistry*, 11, 2958–2967, (1972). Human fibrinogen (98 percent pure/plasmin free) is from American Diagnostica, Greenwich, Connecticut. Radiolabeling of fibrinogen I-2 preparations is performed as previously reported. Smith, et al., *Biochemistry*, 11, 2958–2967, (1972). Urokinase is purchased from Leo Pharmaceuticals, Denmark, as 2200 Ploug units/vial. Streptokinase is purchased from Hoechst-Roussel Pharmaceuticals, Somerville, N.J.

Methods—Effects on Lysis of Human Plasma Clots by t-PA

Human plasma clots are formed in micro test tubes by adding 50 μL thrombin (73 NIH unit/mL) to 100 μL human plasma which contains 0.0229 μCi 125-iodine labeled fibrinogen. Clot lysis is studied by overlaying the clots with 50 μL of urokinase or streptokinase (50, 100, or 1000 unit/mL) and incubating for 20 hours at room temperature. After incubation the tubes are centrifuged in a Beckman Microfuge. 25 μL of supernate is added into 1.0 mL volume of 0.03 M tris/0.15 M NaCl buffer for gamma counting. Counting controls 100 percent lysis are obtained by omitting thrombin (and substituting buffer). The factor Xa inhibitors are evaluated for possible interference with fibrinolysis by including the compounds in the overlay solutions at 1, 5, and 10 μg/mL concentrations. Rough approximations of $IC_{50}$ values are estimated by linear extrapolations from data points to a value which would represent 50 percent of lysis for that particular concentration of fibrinolytic agent.

Anticoagulant Activity Materials

Dog plasma and rat plasma are obtained from conscious mixed-breed hounds (either sex, Butler Farms, Clyde, N.Y., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction I-2 according to previous procedures and specifications. Smith, *Biochem. J.*, 185, 1–11 (1980); and Smith, et al., *Biochemistry*, 11, 2958–2967 (1972). Human fibrinogen is also purchased as 98 percent pure/plasmin free from American Diagnostica, Greenwich, Conn. Coagulation reagents Actin, Thromboplastin, Innovin and Human plasma are from Baxter Healthcare Corp., Dade Division, Miami, Fla. Bovine thrombin from Parke-Davis (Detroit, Mich.) is used for coagulation assays in plasma.

Methods

Anticoagulation Determinations

Coagulation assay procedures are as previously described. Smith, et al., *Thrombosis Research*, 50, 163–174 (1988). A CoAScreener coagulation instrument (American LABor, Inc.) is used for all coagulation assay measurements. The prothrombin time (PT) is measured by adding 0.05 mL saline and 0.05 mL Thromboplastin-C reagent or recombinant human tissue factor reagent (Innovin) to 0.05 mL test plasma. The activated partial thromboplastin time (APTT) is measured by incubation of 0.05 mL test plasma with 0.05 mL Actin reagent for 120 seconds followed by 0.05 mL $CaCl_2$ (0.02 M). The thrombin time (TT) is measured by adding 0.05 mL saline and 0.05 mL thrombin (10 NIH units/mL) to 0.05 mL test plasma. The compounds of formula I are added to human or animal plasma over a wide range of concentrations to determine prolongation effects on the APTT, PT, and TT assays. Linear extrapolations are performed to estimate the concentrations required to double the clotting time for each assay.

Animals

Male Sprague Dawley rats (350–425 gm, Harlan Sprague Dawley Inc., Indianapolis, Ind.) are anesthetized with xylazine (20 mg/kg, s.c.) and ketamine (120 mg/kg, s.c.) and maintained on a heated water blanket (37° C.). The jugular vein(s) is cannulated to allow for infusions.

Arterio-Venous Shunt Model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood is circulated through the shunt for 15 min before the thread is carefully removed and weighed. The weight of a wet thread is subtracted from the total weight of the thread and thrombus (see J. R. Smith, *Br J Pharmacol*, 77:29, 1982).

FeCl$_3$ Model of Arterial Injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. FeCl$_3$ hexahydrate is dissolved in water and the concentration (20 percent) is expressed in terms of the actual weight of FeCl$_3$ only. To injure the artery and induce thrombosis, 2.85 $\mu$L is pipetted into the cuff to bathe the artery above the thermocouple probe. Arterial occlusion is indicated by a rapid drop in temperature. The time to occlusion is reported in minutes and represents the elapsed time between application of FeCl$_3$ and the rapid drop in vessel temperature (see K. D. Kurz, *Thromb. Res.*, 60:269, 1990).

Coagulation Parameters

Plasma thrombin time (TT) and activated partial thromboplastin time (APTT) are measured with a fibrometer. Blood is sampled from a jugular catheter and collected in syringe containing sodium citrate (3.8 percent, 1 part to 9 parts blood). To measure TT, rat plasma (0.1 mL) is mixed with saline (0.1 mL) and bovine thrombin (0.1 mL, 30 U/mL in TRIS buffer; Parke Davis) at 37° C. For APTT, plasma (0.1 mL) and APTT solution (0.1 mL, Organon Teknika) are incubated for 5 minutes (37° C.) and CaCl$_2$ (0.1 mL, 0.025 M) is added to start coagulation. Assays are done in duplicate and averaged.

Index of Bioavailability

Bioavailability studies may be conducted as follows. Compounds are administered as aqueous solutions to male Fisher rats, intravenously (iv) at 5 mg/kg via tail vein injection and orally (po) to fasted animals at 20 mg/kg by gavage. Serial blood samples are obtained at 5, 30, 120, and 240 minutes postdose following intravenous administration and at 1, 2, 4, and 6 hours after oral dosing. Plasma is analyzed for drug concentration using an HPLC procedure involving C8 Bond Elute (Varion) cartridges for sample preparation and a methanol/30 nM ammonium acetate buffer (pH 4) gradient optimized for each compound. % Oral bioavailability is calculated by the following equation:

$$\% \text{ Oral biovailabilty} = \frac{AUC\,po}{AUC\,iv} \times \frac{\text{Dose }iv}{\text{Dose }po} \times 100$$

where AUC is area under the curve calculated from the plasma level of compound over the time course of the experiment following oral (AUC po) and intravenous (AUC iv) dosing.

Compounds

Compound solutions are prepared fresh daily in normal saline and are injected as a bolus or are infused starting 15 minutes before and continuing throughout the experimental perturbation which is 15 minutes in the arteriovenous shunt model and 60 minutes in the FeCl$_3$ model of arterial injury and in the spontaneous thrombolysis model. Bolus injection volume is 1 mL/kg for i.v., and 5 mL/kg for p.o., and infusion volume is 3 mL/hr.

Statistics

Results are expressed as means +/−SEM. One-way analysis of variance is used to detect statistically significant differences and then Dunnett's test is applied to determine which means are different. Significance level for rejection of the null hypothesis of equal means is P<0.05.

Animals

Male dogs (Beagles; 18 months–2 years; 12–13 kg, Marshall Farms, North Rose, N.Y. 14516) are fasted overnight and fed Purina certified Prescription Diet (Purina Mills, St. Louis, Mo.) 240 minutes after dosing. Water is available ad libitum. The room temperature is maintained between 66–74° F.; 45–50 percent relative humidity; and lighted from 0600–1800 hours.

Pharmacokinetic Model

Test compound is formulated immediately prior to dosing by dissolving in sterile 0.9 percent saline to a 5 mg/mL preparation. Dogs are given a single 2 mg/kg dose of test compound by oral gavage. Blood samples (4.5 mL) are taken from the cephalic vein at 0.25, 0.5, 0.75, 1, 2, 3, 4 and 6 hours after dosing. Samples are collected in citrated Vacutainer tubes and kept on ice prior to reduction to plasma, by centrifugation. Plasma samples are analyzed by HPLC MS. Plasma concentration of test compound is recorded and used to calculate the pharmacokinetic parameters: elimination rate constant, Ke; total clearance, Clt; volume of distribution, $V_D$; time of maximum plasma test compound concentration, Tmax; maximum concentration of test compound of Tmax, Cmax; plasma half-life, t0.5; and area under the curve, A.U.C.; fraction of test compound absorbed, F.

Canine Model of Coronary Artery Thrombosis

Surgical preparation and instrumentation of the dogs are as described in Jackson, et al., *Circulation*, 82, 930–940 (1990). Mixed-breed hounds (aged 6–7 months, either sex, Butler Farms, Clyde, N.Y., U.S.A.) are anesthetized with sodium pentobarbital (30 mg/kg intravenously, i.v.), intubated, and ventilated with room air. Tidal volume and respiratory rates are adjusted to maintain blood $PO_2$, $PCO_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model (MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left circumflex coronary artery (LCX) is isolated proximal to the first major diagonal ventric,ular branch. A 26-gauge needle-tipped wire anodal electrode (Teflon-coated, 30-gauge silverplated copper wire) 3–4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40–50 percent inhibition of the hyperemic blood flow response observed after 10-s mechanical occlusion of the LCX. All hemodynamic and ECG measurements are recorded and analyzed with a data acquisition system (model M3000, Modular Instruments, Malvern, Pa. U.S.A.).

Thrombus Formation and Compound Administration Regimens

Electrolytic injury of the intima of the LCX is produced by applying 100-$\mu$A direct current (DC) to the anode. The current is maintained for 60 min and then discontinued whether the vessel has occluded or not. Thrombus formation proceeds spontaneously until the LCX is totally occluded (determined as zero CBF and an increase in the S-T segment). Compound administration is started after the occluding thrombus is allowed to age for 1 hour. A 2-hour infusion of the compounds of the present invention at doses of 0.5 and 1 mg/kg/hour is begun simultaneously with an infusion of thrombolytic agent (e.g. tissue plasminogen activator, streptokinase, APSAC). Reperfusion is followed for 3 hour after administration of test compound. Reocclusion of coronary arteries after successful thrombolysis is defined as zero CBF which persisted for at least 30 minutes.

Hematology and Template Bleeding Time Determinations

Whole blood cell counts, hemoglobin, and hematocrit values are determined on a 40-$\mu$L sample of citrated (3.8 percent) blood (1 part citrate:9 parts blood) with a hematology analyzer (Cell-Dyn 900, Sequoia-Turner. Mount View, Calif., U.S.A.). Gingival template bleeding times are determined with a Simplate II bleeding time device (Organon Teknika Durham, N.C., U.S.A.). The device is used to make 2 horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 min), 60 min into infusion, at conclusion of administration of the test compound (120 min), and at the end of the experiment.

All data are analyzed by one-way analysis of variance (ANOVA) followed by Student-Neuman-Kuels post hoc t test to determine the level of significance. Repeated-measures ANOVA are used to determine significant differences between time points during the experiments. Values are determined to be statistically different at least at the level of $p<0.05$. All values are mean±SEM. All studies are conducted in accordance with the guiding principles of the American Physiological Society. Further details regarding the procedures are described in Jackson, et al., *J. Cardiovasc. Pharmacol.*, (1993), 21, 587–599.

The following Examples are provided to further describe the invention and are not to be construed as limitations thereof.

The abbreviations, symbols and terms used in the examples have the following meanings.

Ac=acetyl
aq=aqueous
Bn or Bzl=benzyl
Boc=t-butyloxycarbonyl
Bu=butyl
n-BuLi=butyllithium
Calcd=calculated
conc=concentrated
DMF=dimethylformamide
DMSO=dimethylsulfoxide
eq=(molar) equivalent
Et=ethyl
EtOAc=ethyl acetate
$Et_3N$=triethylamine
$Et_2O$=diethyl ether
EtOH=ethanol
FTIR=Fourier transform IR
Hex=hexanes
HPLC=High Performance Liquid Chromatography
HRMS=high resolution mass spectrum
i-PrOH=isopropanol
IR=Infrared Spectrum
LC-MS=liquid chromatography—mass spectrum (using HPLC)
Me=methyl
MeOH=methanol
MS-ES (or ES-MS)=electrospray mass spectrum
MS-FAB (or FAB-MS)=fast atom bombardment mass spectrum
MS-FIA (or FIA-MS)=flow injection analysis mass spectrum
MS-FD (or FD-MS)=field desorption mass spectrum
MS-IS (or IS-MS)=ion spray mass spectrum
NMR=Nuclear Magnetic Resonance
Ph=phenyl
i-Pr=isopropyl RPHPLC=Reversed Phase High Performance Liquid Chromatography
RT (or $R_t$)=retention time
satd=saturated
$SiO_2$=silica gel
SCX=strong cation exchange (resin)
TBS=tert-butyldimethylsilyl
TFA=trifluoroacetic acid
THF=tetrahydrofuran
TIPS=triisopropylsilyl
TLC=thin layer chromatography
tosyl=p-toluenesulfonyl
triflic acid=trifluoromethanesulfonic acid Unless otherwise stated, pH adjustments and work up are with aqueous acid or base solutions. $^1$H-NMR indicates a satisfactory NMR spectrum was obtained for the compound described. IR (or FTIR) indicates a satisfactory infra red spectrum was obtained for the compound described.

For consistency and clarity, a number of compounds are named as substituted pyridinecarboxamide or pyrazinecarboxamide derivatives.

EXAMPLE 1

Preparation of N-(6-Chloropyridin-3-yl)-2-[[1-(4-pyridinyl)-piperidin-4-ylmethyl]amino]pyridine-3-carboxamide Dihydrochloride

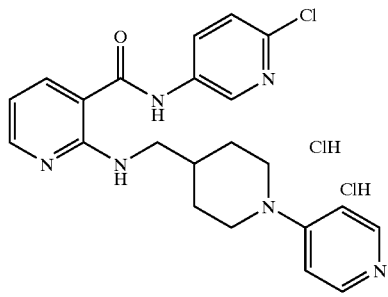

A. 1-(4-Pyridinyl)piperidine-4-methylamine.

1-(4-Pyridinyl)piperidine-4-methanol was prepared using a procedure similar to the following: A solution of methyl N-(4-pyridinyl)isonipecotate (600 mg, 2.72 mmol) in tetrahydrofuran was added to a solution of lithium aluminum hydride (100 mg) in tetrahydrofuran (14 mL) cooled to 0° C. Upon consumption of the starting material (0.5–2 h), the mixture was treated with water (0.10 mL), 15% aqueous sodium hydroxide (0.10 mL), and water (0.30 mL). After 0.25 h, the mixture was sonicated for 0.25 h, then poured into a mixture of ethyl acetate, water, sodium tartrate, and potassium tartrate. The aqueous layer was extracted twice with ethyl acetate and the combined extracts were dried (magnesium sulfate), filtered, and concentrated in vacuo to yield 357 mg (68%) of 1-(4-pyridinyl)piperidine-4-methanol, which was used without further purification.

$^1$H-NMR

A solution of 1-(4-pyridinyl)piperidine-4-methanol (5.87 g, 30.6 mmol), phthalimide (4.59 g, 31.2 mmol), and triphenylphosphine (8.10 g, 30.9 mmol) in 125 mL of THF at −5° C. was treated with a solution of diethyl azodicarboxylate (5.38 g, 30.9 mmol) in THF (40 mL). After 16 h, the mixture was poured into EtOAc and 1 N HCl. The aqueous layer was washed with EtOAc (2×), pH adjusted to 12 by addition of 5 N NaOH, and washed with EtOAc (3×). The combined organic extracts were dried ($K_2CO_3$) and concentrated yielding 8.45 g (86%). The crude material (5.47 g, 17.0 mmol) was then treated with hydrazine hydrate (3.5 mL, 60.0 mmol) in EtOH (50 mL). The mixture was heated at 75° C. for 5 h, cooled, diluted with $CH_2Cl_2$ (100 mL), and cooled to 0° C. The solid was removed by filtration and the filtrate was concentrated yielding 3.32 g of the title compound which was used without further purification.

$^1$H-NMR, IR; FD-MS, m/e 191 (m).

B. Ammonium 2-[[1-(4-Pyridinyl)piperidin-4-ylmethyl]-amino]pyridine-3-carboxylate.

A mixture of 2-chloronicotinic acid (10.74 g, 67.5 mmol), 1-(4-pyridinyl)piperidin-4-methylamine (8.60 g, 45.0 mmol), and potassium carbonate (15.5 g, 112.6 mmol) in dimethylformamide (90 mL) was heated at reflux. After 16 h, the mixture was diluted with methanol, filtered, and concentrated. The residue was dissolved in methanol, acidified with 1 N HCl in ether, heated at reflux for 0.25 h, cooled and the solid removed by filtration. The filtrate was then treated with 2 M $NH_3$ in methanol until slightly basic, triturated with THF and the resulting solid collected by filtration yielding 10.75 g of the title compound; which was used without further purification.

$^1$H-NMR; IS-MS, m/e 313 (m+1).

C. N-(6-Chloropyridin-3-yl)-2-[[1-(4-pyridinyl)piperidin-4-ylmethyl]amino]pyridine-3-carboxamide.

A solution of ammonium 2-[[1-(4-pyridinyl)piperidin-4-ylmethyl]amino]pyridine-3-carboxylate (3.0 g, 9.12 mmol) in dioxane (45 mL) was treated with phosgene (1.9 M in toluene, 9.50 mL, 18.2 mmol), and the resulting mixture was heated at reflux. After 2 h, the mixture was concentrated yielding the corresponding aza-isatoic anhydride which was used without further purification. A solution of the crude anhydride (300 mg, 0.648 mmol) in tetrahydrofuran (2 mL) at 0° C. was treated with the magnesium salt of 2-amino-5-chloropyridine [2.60 mmol; freshly prepared by addition of methyl magnesium bromide (3.0 M in THF, 0.865 mL, 2.60 mmol) to 2-amino-5-chloropyridine (900 mg, 3.89 mmol) in THF (10 mL) at 0° C.]. After 17 h, the mixture was treated with a saturated aqueous solution of ammonium chloride and then partitioned between EtOAc and water. The aqueous layer was washed with EtOAc (3×) and the combined extracts were washed with water (1×), dried with sodium sulfate, and concentrated. The residue was purified by RPHPLC yielding 29 mg (9%) of the title compound as a hydrochloride salt.

$^1$H-NMR; IS-MS, m/e (m). Analysis for $C_{22}H_{23}ClN_6O\cdot2.0\ HCl\cdot1.8\ H_2O$: Calcd: C, 50.22; H, 5.10; N, 15.97; Found: C, 50.48; H, 5.10; N, 15.67.

EXAMPLE 2

Preparation of N-(5-Chloropyridin-2-yl)-3-[[1-(4-pyridinyl)piperidin-4-ylcarbonyl]amino]pyridine-2-carboxamide Hydrochloride

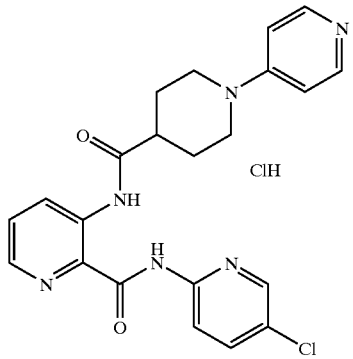

A. 3-Aminopyridine-N-(5-chloropyridin-2-yl)-2-carboxamide.

A (Parr) pressure apparatus was charged with 3-amino-2-chloropyridine (500 mg, 3.89 mmol), 2-amino-5-chloropyridine (1.00 g, 7.78 mmol), palladium acetate (88 mg, 0.39 mmol), 1,3-bis(diphenylphosphino)propane (483 mg, 1.17 mmol) and triethylamine (590 mg, 5.84 mmol). The mixture was placed under a carbon monoxide atmosphere (4.1 bar) and heated at 100° C. After 72 h, the mixture was filtered, concentrated and the residue purified by column chromatography (SiO$_2$: 0 to 5% EtOAc in methylene chloride) affording 550 mg (57%) of the title compound.

$^1$H-NMR, IR; IS-MS, m/e 249 (m); Analysis for C$_{11}$H$_9$ClN$_4$O:

| | | | |
|---|---|---|---|
| Calcd: | C, 53.13; | H, 3.65; | N, 22.53; |
| Found: | C, 53.40; | H, 3.66; | N, 22.45. |

B. N-(5-Chloropyridin-2-yl)-3-[[1-(4-pyridinyl)piperidin-4-ylcarbonyl]amino]pyridine-2-carboxamide Hydrochloride.

3-Aminopyridine-N-(5-chloropyridin-2-yl)-2-carboxamide (5.73 g, 23.0 mmol) was added to a solution of pyridine (3.92 mL) and 1-(4-pyridinyl)piperidin-4-yl carbonyl chloride (24.2 mmol, prepared by addition of oxalyl chloride [26.7 mmol] to sodium 1-(4-pyridinyl)piperidine-4-carboxylate [24.2 mmol]) in methylene chloride. After 16 h, the mixture was partitioned between saturated sodium bicarbonate and methylene chloride. The organic layer was dried with magnesium sulfate, filtered, concentrated, and the residue purified by column chromatography (SiO$_2$; 5 to 10% methanol: methylene chloride) followed by recrystallization from EtOAc:hexanes and treatment with hydrochloric acid to yield 842 mg (8%) of the title compound.

$^1$H-NMR, IR; Analysis for C$_{22}$H$_{21}$ClN$_6$O$_2$.1.75 HCl:

| | | | |
|---|---|---|---|
| Calcd: | C, 52.77; | H, 4.57; | N, 16.78; |
| Found: | C, 52.93; | H, 4.63; | N, 16.74. |

EXAMPLE 3

Preparation of 3-[(4-tert-Butylbenzoyl)amino]-N-(5-chloro-pyridin-2-yl)pyrazine-2-carboxamide

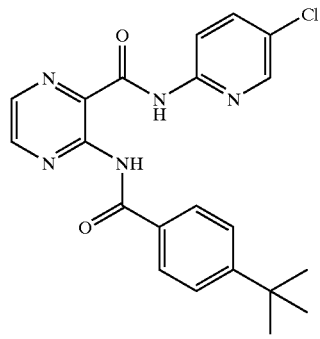

A. 3-Amino-N-(5-chloropyridin-2-yl)pyrazine-2-carboxamide.

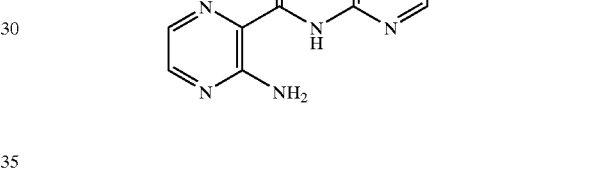

To a cold (0° C.) solution of 3-aminopyrazine-2-carboxylic acid (10 g, 72 mmol) in CH$_2$Cl$_2$ (250 mL) was added a 2 M solution of oxalyl chloride (43 mL, 86 mmol) in CH$_2$Cl$_2$ followed by DMF (10 mL) dropwise. The cooling bath was removed, and the reaction was stirred for 2 hours at ambient temperature. It was recooled to 0° C. and treated with a 0° C. solution of 2-amino-5-chloropyridine (12 g, 94 mmol) and pyridine (32 mL) in CH$_2$Cl$_2$ (200 mL). The cooling bath was removed and the reaction was stirred overnight at ambient temperature. The mixture was concentrated to dryness in vacuo and the residue was mixed with MeOH. The solid was filtered to recover 15.6 g (87%) of product.

$^1$H-NMR; MS, m/e 249 (m); Analysis for C$_{10}$H$_8$N$_5$O.0.3H$_2$O:

| | | | |
|---|---|---|---|
| Calcd: | C, 47.09; | H, 3.40; | N, 27.46; |
| Found: | C, 47.38; | H, 3.24; | N, 27.14. |

B. 3-[(4-tert-Butylbenzoyl)amino]-N-(5-chloropyridin-2-yl)pyrazine-2-carboxamide.

To a mixture of the above 3-amino-N-(5-chloropyridin-2-yl)pyrazine-2-carboxamide (255 mg, 1 mmol) in pyridine (20 mL) was added 4-tert-butylbenzoyl chloride (402 mg, 86 mmol). The mixture was stirred for 36 hours at 55° C. It was cooled to room temperature then concentrated to dryness in vacuo. The residue was mixed with $CH_2Cl_2$ and purified by radial chromatography from which was recovered 85 mg (21%) of product.

$^1$H-NMR; MS, m/e 410 (m+1); Analysis for $C_{21}H_{20}ClN_5O_2$:

| Calcd: | C, 61.54; | H, 4.92; | N, 17.09; |
|---|---|---|---|
| Found: | C, 61.84; | H, 5.09; | N, 17.32. |

EXAMPLE 4

Preparation of N-(6-Chlorobenzothiazol-2-yl)-2-[[1-(4-pyridinyl)piperidin-4-ylmethyl]amino]pyridine-3-carboxamide

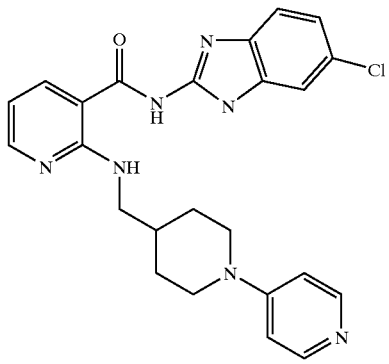

A solution of ammonium 2-[[1-(4-pyridinyl)piperidin-4-ylmethyl]amino]pyridine-3-carboxylate (400 mg, 1.28 mmol) in methylene chloride (5 mL) was treated with thionyl chloride (0.112 mL, 1.54 mmol) and the mixture was heated at reflux. After 3 h, the mixture was cooled and then treated dropwise with a solution of 2-amino-6-chlorobenzothiazole (284 mg, 1.54 mmol) in pyridine (5 mL). After 1 h, the mixture was concentrated in the presence of silica gel. The residue was purified by column chromatography (SiO$_2$: 1 to 4% [2 N ammonia in methanol]:chloroform) followed by recrystallization from methanol to yield 68 mg (11%) of the title compound.

$^1$H-NMR; IS-MS, m/e 480 (m+1); Analysis for $C_{24}H_{23}ClN_6OS$:

| Calcd: | C, 60.18; | H, 4.84; | N, 17.54; |
|---|---|---|---|
| Found: | C, 60.41; | H, 4.98; | N, 17.56. |

EXAMPLE 5

Preparation of N-(5-Chloropyridin-2-yl)-2-[[1-(4-pyridinyl)piperidin-4-ylcarbonyl]amino]pyridine-3-carboxamide Hydrochloride

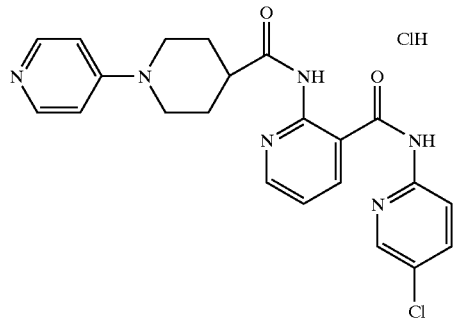

A. 2-Amino-N-(5-Chloropyridin-2-yl)pyridine-3-carboxamide Hydrochloride.

To a stirring suspension of 2-aminonicotinic acid (26.9 g, 194 mmol) in dichloromethane (120 mL) at 0° C., was added DMF (a few drops) followed by oxalyl chloride (20 mL, 194 mmol). The cold bath was removed and the solution was allow,ed to stir for 60 min at room temperature. This solution was then transferred via cannula into a stirring solution of 2-amino-5-chloropyridine (25 g, 194 mmol) and pyridine (78 mL, 970 mmol) in dichloromethane (100 mL). After stirring overnight, the precipitate was filtered and dried to give 32.8 g of solid. The crude product was recrystalized from ethanol with activated charcoal to give 12.4 g (23%) of white solid.

$^1$H-NMR; IS-MS, m/e 249.0 (m+1); Analysis for $C_{11}H_9N_4OCl.HCl$:

| Calcd: | C, 46.33; | H, 3.54; | N, 19.65; | Cl, 24.87; |
|---|---|---|---|---|
| Found: | C, 46.64; | H, 3.42; | N, 19.63; | Cl, 25.23. |

B. N-(5-Chloropyridin-2-yl)-2-[[1-(4-pyridinyl)piperidin-4-ylcarbonyl]amino]pyridine-3-carboxamide Hydrochloride.

By methods substantially equivalent to those described in example 2-B, N-(5-chloropyridin-2-yl)-2-[[1-(4-pyridinyl)piperidin-4-ylcarbonyl]amino]pyridine-3-carboxamide hydrochloride (84 mg, 4%) was prepared from 2-amino-N-(5-chloropyridin-2-yl)pyridine-3-carboxamide and 1-(4-pyridinyl)piperidine-4-carbonyl chloride. The compound was purified by preparative RPHPLC (C18), eluting with a linear gradient of 90/10 to 50/50 (0.01% HCl/acetonitrile) over 180 min.

$^1$H-NMR; IS-MS, m/e 437.2 (m+1).

EXAMPLE 6

Preparation of N-(5-Chloropyridin-2-yl)-3-[(1-isopropylpiperidin-4-ylcarbonyl)amino]pyridine-2-carboxamide Hydrochloride

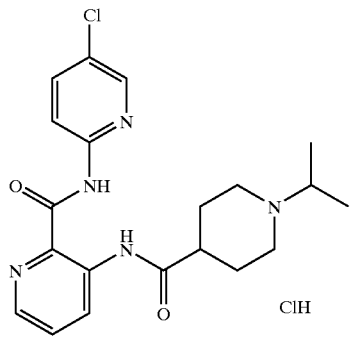

A. N-(5-Chloropyridin-2-yl)-3-[(1-Boc-piperidin-4-ylcarbonyl)amino]pyridine-2-carboxamide.

To a stirring solution of Boc-isonipecotic acid (15.4 g, 67 mmol) in THF (200 mL) was added sodium methoxide (3.62 g, 67 mmol). After stirring for 1 h, the solvent was removed in vacuo and the dry residue was suspended in dichloromethane (100 mL). To this stirring suspension was added a few drops of DMF followed by oxalyl chloride (6.5 mL, 74 mmol). After stirring for 2 h, the solvents were removed in vacuo and the residue was diluted to a volume of about 130 mL with dichloromethane.

A portion of this solution (81 mL, 40 mmol) was added via syringe to a stirring solution of N-(5-chloropyridin-2-yl)-3-aminopyridine-2-carboxamide (6.7 g, 26.9 mmol), 4-dimethylaminopyridine (0.49 g, 4 mmol) and N,N-diisopropylethylamine (8.2 mL, 47.1 mmol) in dichlqromethane (200 mL). After stirring overnight, the solvent was removed in vacuo and the residue was partitioned between ethyl acetate and water. The phases were separated and the organic phase was washed consecutively with 0.5 M citric acid (2×), brine, sat. aq. sodium bicarbonate (2×), and brine. The solution was then dried with $MgSO_4$, filtered, concentrated in vacuo, and the residue was chromatographed over silica gel, eluting with dichloromethane, followed by 10% ethyl acetate in dichloromethane. The product containing fractions were combined and concentrated in vacuo to give 8.69 g (72%) of a white solid.

$^1$H-NMR; IS-MS, m/e 460.4 (m+1).

B. N-(5-Chloropyridin-2-yl)-3-[(piperidin-4-ylcarbonyl)amino]pyridine-2-carboxamide Trifluoroacetate.

To a stirring solution of N-(5-chloropyridin-2-yl)-3-[(1-Boc-piperidin-4-ylcarbonyl)amino]pyridine-2-carboxamide (8.5 g, 18.5 mmol) and anisole (20 mL) in dichloromethane (150 mL) was added TFA (150 mL). After stirring for 1 h, the solvent was removed in vacuo and the residue was suspended in diethyl ether with vigorous stirring. After 30 min, the solid was filtered, washed several times with diethyl ether and then dried in vacuo to give 8.53 g (97%) of a white solid.

$^1$H-NMR; IS-MS, m/e 360.2 (m+1); Analysis for $C_{17}H_{18}ClN_5O_2$:

| Calcd: | C, 47.52; | H, 3.97; | N, 14.43; | F, 12.92; |
|---|---|---|---|---|
| Found: | C, 47.81; | H, 3.98; | N, 14.36; | F, 12.76. |

C. N-(5-Chloropyridin-2-yl)-3-[(1-isopropylpiperidin-4-ylcarbonyl)amino]pyridine-2-carboxamide Hydrochloride.

To a stirring suspension of N-(5-chloropyridin-2-yl)-3-[(piperidin-4-ylcarbonyl)amino]pyridine-2-carboxamide trifluoroacetate (0.34 g, 0.72 mmol) in 1,2-dichloroethane (10 mL) was added acetone (10 mL), followed by acetic acid (0.7 mL, 2.88 mmol) and then sodium triacetoxyborohydride (0.61 g, 2.88 mmol). After stirring overnight, the solution was loaded onto an SCX column (prewashed with 5% acetic acid in methanol) and washed with methanol. The product was then eluted from the column with a 2 N solution of ammonia in methanol. The product containing fractions were concentrated in vacuo and the compound was purified by preparative RPHPLC (C18), eluting with a linear gradient of 90/10 to 50/50 (0.01% HCl/acetonitrile) over 180 min, to give 0.14 g (44%) of a white solid.

$^1$H-NMR; IS-MS, m/e 402.3 (m+1); Analysis for $C_{20}H_{24}N_5O_2Cl.1.0HCl.1.5H_2O$:

| Calcd: | C, 51.62; | H, 6.06; | N, 15.05; | Cl, 15.24; |
|---|---|---|---|---|
| Found: | C, 51.61; | H, 5.75; | N, 14.80; | Cl, 15.31. |

EXAMPLE 7

Preparation of N-(5-Methylpyridin-2-yl)-2-[[1-(4-pyridinyl)piperidin-4-ylmethyl]amino]pyridine-3-carboxamide Dihydrochloride

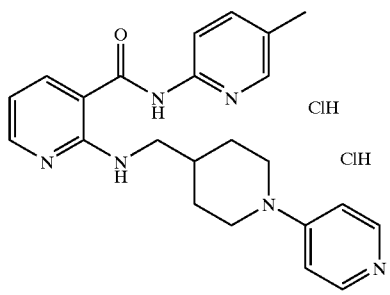

Using a similar procedure to that described in Example 1-C, the crude anhydride (300 mg, 0.648 mmol) and 2-amino-5-methylpyridine (280 mg, 2.60 mmol) yielded 64 mg (20%) of the title compound as a hydrochloride salt.

$^1$H-NMR, IR; IS-MS, m/e 403 (m+1); Analysis for $C_{23}H_{26}N_6O.-2.0$ HCl:

| Calcd: | C, 58.11; | H, 5.94; | N, 17.68; |
|---|---|---|---|
| Found: | C, 58.35; | H, 5.85; | N, 17.60. |

EXAMPLE 8

Preparation of N-(6-Chloropyridazin-3-yl)-2-[[1-(4-pyridinyl)piperidin-4-ylmethyl]amino]pyridine-3-carboxamide Dihydrochloride

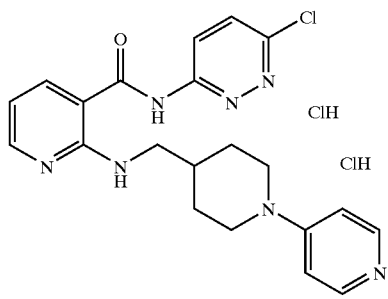

Using a similar procedure to that described in Example 1-C, the crude anhydride (300 mg, 0.648 mmol) and 3-amino-5-chloropyridazine (335 mg, 2.60 mmol) yielded 46 mg (14%) of the title compound as a hydrochloride salt.

$^1$H-NMR; IS-MS, m/e 424 (m+1).

EXAMPLE 9

Preparation of N-(Benzothiazol-2-yl)-2-[[1-(4-pyridinyl)piperidin-4-ylmethyl]amino]pyridine-3-carboxamide Dihydrochloride

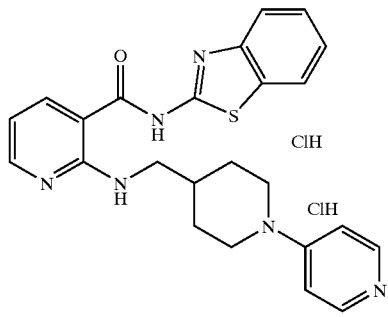

Using a similar procedure to that described in Example 1-C, the crude anhydride (300 mg, 0.648 mmol) and 2-aminobenzothiazole (390 mg, 2.60 mmol) yielded 70 mg (24%) of the title compound as a hydrochloride salt.

$^1$H-NMR; IS-MS, m/e 445 (m+1); Analysis for $C_{24}H_{24}N_6OS \cdot 3.0$ HCl, 1.5 $H_2O$:

| | | | |
|---|---|---|---|
| Calcd: | C, 49.78; | H, 5.19; | N, 14.51; |
| Found: | C, 49.63; | H, 4.76; | N, 14.22. |

EXAMPLE 10

Preparation of N-(6-Methylbenzothiazol-2-yl)-2-[[1-(4-pyridinyl)piperidin-4-ylmethyl]amino]pyridine-3-carboxamide Dihydrochloride

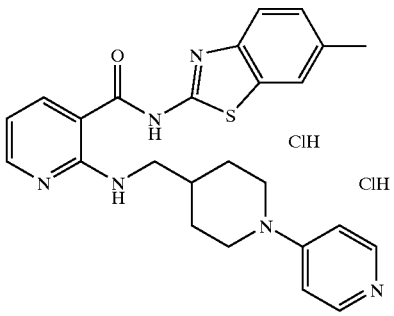

Using a similar procedure to that described in Example 1-C, the crude anhydride (300 mg, 0.648 mmol) and 2-amino-6-methylbenzothiazole (426 mg, 2.60 mmol) yielded 66 mg (19%) of the title compound as a hydrochloride salt.

$^1$H-NMR; IS-MS, m/e 445 (m+1); Analysis for $C_{25}H_{26}N_6OS \cdot 3.0$ HCl $\cdot 1.0$ $H_2O$:

| | | | |
|---|---|---|---|
| Calcd: | C, 51.25; | H, 5.33; | N, 14.34; |
| Found: | C, 51.51; | H, 5.14; | N, 14.28. |

EXAMPLE 11

Preparation of N-(6-Bromobenzothiazol-2-yl)-2-[[1-(4-pyridinyl)piperidin-4-ylmethyl]amino]pyridine-3-carboxamide Dihydrochloride

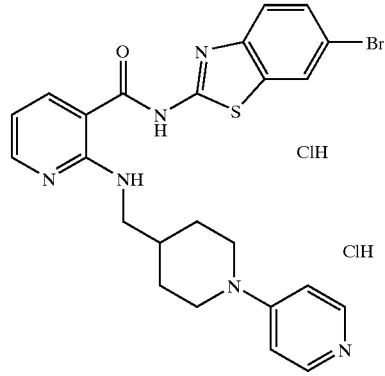

Using a similar procedure to that described in Example 1-C, the crude anhydride (300 mg, 0.648 mmol) and 2-amino-6-bromobenzothiazole (595 mg, 2.60 mmol) yielded 8.0 mg (2%) of the title compound as a hydrochloride salt.

$^1$H-NMR; IS-MS, m/e 524 (m+1).

EXAMPLE 12

Preparation of N-(5-Chloropyrimindin-2-yl)-2-[[1-(4-pyridinyl)piperidin-4-ylmethyl]amino]pyridine-3-carboxamide Dihydrochloride

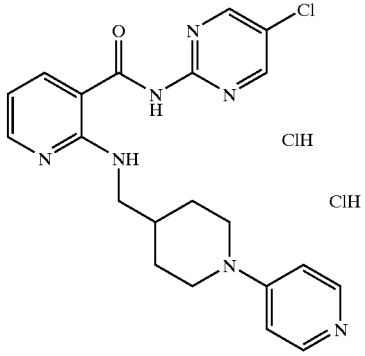

Using a similar procedure to that described in Example 1-C, the crude anhydride (300 mg, 0.648 mmol) and 2-amino-5-chloropyrimidine (595 mg, 2.60 mmol) yielded 8.0 mg (2%) of the title compound as a hydrochloride salt.

$^1$H-NMR; IS-MS, m/e 524 (m+1).

EXAMPLE 13

Preparation of N-(5-Chloropyridin-2-yl)-2-[(1-isopropylpiperidin-4-ylmethyl)amino]pyridine-2-carboxamide

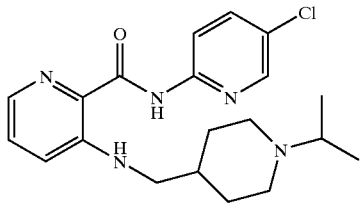

A. 1-tert-Butoxycarbonylpiperidine-4-methanol.

A solution of 1-tert-butoxycarbonyl isonipecotic acid (40 g, 0.17 mol) and N-methylmorpholine (19 mL, 0.17 mol) in tetrahydrofuran (900 mL) at −10° C. was treated with ethyl chloroformate (17 mL, 0.17 mol). After 0.5 h, sodium borohydride was added (19.8 g, 0.5 mol) in one portion followed by slow addition of methanol. After gas evolution ceased, the mixture was concentrated and the residue was diluted with 10% aqueous acetic acid and partitioned between ethyl acetate and water. The aqueous layer was washed with EtOAc (2×) and the combined organic extracts were dried with magnesium sulfate, filtered, and concentrated to a solid residue which was purified by column chromatography (SiO$_2$: 10 to 50% EtOAc:hexanes) providing the title compound (33.8 g, 90%) as a white solid.

$^1$H-NMR.

B. 1-tert-Butoxycarbonylpiperidine-4-carboxaldehyde.

A solution of oxalyl chloride (6 mL, 70 mmol) in dichloromethane (60 mL) at −78° C. was treated dropwise with dimethyl sulfoxide (10 mL, 0.14 mol). After 15 minutes, 1-tert-butoxycarbonylpiperidine-4-methanol (3.0 g, 14 mmol) was added as a solution in dichloromethane (35 mL). The mixture was stirred at −78° C. for 1 h, then triethylamine (29 mL, 0.21 mol) was added dropwise. The mixture was warmed to ambient temperature and poured into saturated ammonium chloride solution (200 mL). The organic layer was separated and the aqueous layer was washed with dichloromethane (75 mL). The organic layers were combined and washed with brine (75 mL), then dried with MgSO$_4$, filtered and concentrated. The residue was redissolved in ethyl acetate-hexanes (1:1) and filtered through Florisil (100–200 mesh). The resulting filtrate was concentrated yielding 3.0 g (100%) of the title aldehyde as a yellow oil; which was used without further purification.

$^1$H-NMR.

C. N-(5-Chloropyridin-2-yl)-3-[(1-Boc-piperidin-4-ylmethylidine)amino]pyridine-2-carboxamide.

A solution containing 1-tert-butoxycarbonylpiperidine-4-carboxaldehyde (2.00 g, 9.38 mmol), 3-amino-N-(5-chloropyridin-2-yl)pyridine-2-carboxamide (2.33 g, 9.38 mmol), and pyridinium p-toluenesulfonate (236 mg, 0.94 mmol) in benzene (100 mL) was heated at reflux with azeotropic removal of water. After 48 h, the mixture was concentrated and the residue was purified by column chromatography (SiO$_2$: methylene chloride) yielding the title compound, which was contaminated with 3-amino-N-(5-chloropyridin-2-yl)pyridine-2-carboxamide and was used without further purification.

$^1$H-NMR; IS-MS, m/e 444(m).

D. N-(5-Chloropyridin-2-yl)-3-[(piperidin-4-ylmethyl)amino]pyridine-2-carboxamide.

A solution containing N-(5-chloropyridin-2-yl)-3-[(1-Boc-piperidin-4-ylmethylidine)amino]pyridine-2-arboxamide (crude obtained from Part C) and borane trimethylamine complex (2.05 g, 28.14 mmol) in glacial acetic acid was heated at reflux for 2 h. The mixture was cooled, concentrated, and the residue was dissolved in methanol (100 mL) and 12 N HCl (10 mL). After 24 h, the mixture was concentrated, the residue was partitioned between EtOAc and water, and the organic layer washed with a saturated potassium carbonate solution. The organic layer was dried with magnesium sulfate, filtered, concentrated, and the residue was purified by column chromatography (SiO$_2$: 10% [2 N ammonia in methanol]:methylene chloride) yielding 1.63 g (50%) of the title compound.

$^1$H-NMR, IR; IS-MS, m/e 346 (m); Analysis for C$_{17}$H$_{20}$ClN$_5$O:

| Calcd: | C, 59.04; | H, 5.83; | N, 20.25; |
| Found: | C, 58.76; | H, 5.84; | N, 20.05. |

E. N-(5-Chloropyridin-2-yl)-2-[(1-isopropylpiperidin-4-ylmethyl)amino]pyridine-2-carboxamide.

A solution of N-(5-chloropyridin-2-yl)-3-[(piperidin-4-ylmethyl)amino]pyridine-2-carboxamide (100 mg, 0.29 mmol), acetone (1 mL), and anhydrous magnesium sulfate (500 mg) in 95:5 methanol:acetic acid (10 mL) was treated with sodium cyanoborohydride (73 mg, 1.16 mmol). After 4 days, the mixture was filtered, concentrated, and the residue purified by column chromatography (SiO$_2$: 1 to 20% methanol:methylene chloride) yielding 100 mg (89%) of the title compound.

$^1$H-NMR, IR; IS-MS, m/e 388(m+1); Analysis for C$_{20}$H$_{26}$ClN$_5$O.0.25 H$_2$O:

| Calcd: | C, 61.22; | H, 6.81; | N, 17.25; |
| Found: | C, 61.35; | H, 6.46; | N, 17.20. |

EXAMPLE 14

Preparation of 5-Chloro-N-(5-chloropyridin-2-yl)-2-[[1-(4-pyridinyl)piperidin-4-ylmethyl]amino]pyridine-3-carboxamide Tetrahydrochloride

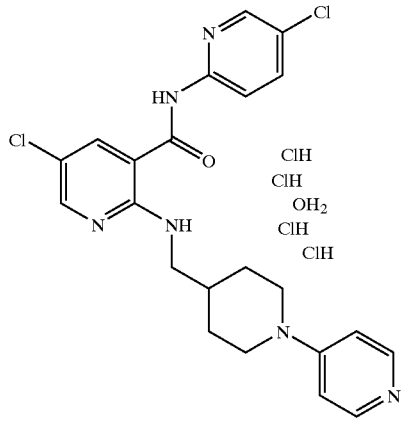

A. N-(5-Chloropyridin-2-yl)-2,5-dichloropyridine-3-carboxamide.

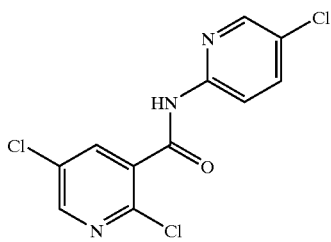

To a ice cooled solution of 2-amino-5-chloropyridine (20 g, 95 mmol) in dichloromethane (200 mL) and pyridine (20 mL) was added 2,5-dichloronicotinoyl chloride (11.58 g, 90 mmol) dropwise. The reaction mixture was warmed to room temperature and stirred overnight. The solvent was evaporated and the residue was partitioned between ethyl acetate (500 mL) and water (100 mL). The aqueous layer was extracted with ethyl acetate (3×100 mL). Combined organic layers, and washed with water (100 mL), saturated citric acid solution (2×100 mL), saturated sodium bicarbonate (2×100 mL) and water (200 mL). Dried over magnesium sulfate and evaporated off the solvent. The residue was slurried with ether (100 mL), and the off-white solids were collected by filtration (24 g, 88%).

$^1$H-NMR; FD-MS, m/e 302.1 (m+1); Analysis for $C_{11}H_6Cl_3N_3O$:

| Calcd: | C, 43.67; | H, 2.0; | N, 13.89; |
|---|---|---|---|
| Found: | C, 43.97; | H, 1.88; | N, 13.97. |

B. 5-Chloro-N-(5-chloropyridin-2-yl)-2-[[1-(4-pyridinyl)piperidin-4-ylmethyl]amino]pyridine-3-carboxamide Tetrahydrochloride.

A suspension of N-(5-chloropyridin-2-yl)-2,5-dichloropyridine-3-carboxamide (0.807 g, 2.68 mmol) and 1-(4-pyridinyl)piperidine-4-methylamine (510 mg) in ethyl alcohol (5 mL) was heated in a sealed tube for 24 hours. Filtered the solids and purified by RPHPLC. The pure product containing fractions were combined and lyophilized to give 0.1 g of an off-white solid.

$^1$H-NMR; FD-MS, m/e 457.4 (m+1); Analysis for $C_{22}H_{22}Cl_2N_6O.4HCl.H_2O$:

| Calcd: | C, 42.54; | H, 4.54; | N, 13.53; |
|---|---|---|---|
| Found: | C, 42.95; | H, 4.57; | N, 13.58. |

EXAMPLE 15

Preparation of N-(5-Chloropyridin-2-yl)-3-[[1-(tetrahydropyran-4-yl)piperidin-4-ylcarbonyl]amino]pyridine-2-carboxarmide Hydrochloride

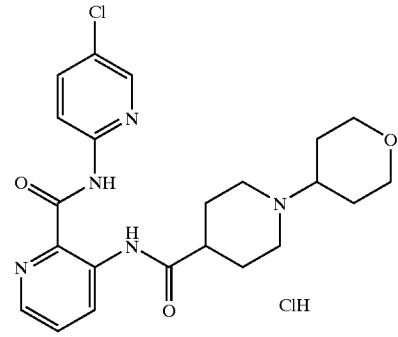

By methods substantially equivalent to those described in example 6-C, N-(5-chloropyridin-2-yl)-3-[[1-(tetrahydropyran-4-yl)piperidin-4-ylcarbonyl]amino]pyridine-2-carboxamide hydrochloride (0.138 g, 34%) was prepared from N-(5-chloropyridin-2-yl)-3-[(piperidin-4-ylcarbonyl)amino]-pyridine-2-carboxamide trifluoroacetate and tetrahydropyran-4-one. The compound was purified by preparative RPHPLC (C18), eluting with a linear gradient of 80/20 to 50/50 (0.01% HCl/acetonitrile) over 180 min.

$^1$H-NMR; IS-MS, m/e 444.2 (m+1); Analysis for $C_{22}H_{26}N_5O_3Cl.1.2HCl.1.0H_2O$:

| Calcd: | C, 52.25; | H, 5.82; | N, 13.85; | Cl, 15.42; |
|---|---|---|---|---|
| Found: | C, 52.18; | H, 5.48; | N, 13.97; | Cl, 15.27. |

EXAMPLE 16

Preparation of N-(5-Chloropyridin-2-yl)-2-[(1-cyclopentylpiperidin-4-ylmethyl)aminojpyridine-2-carboxamide

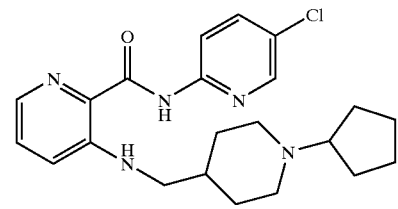

Using a similar procedure to that described in Example 13-E, N-(5-chloropyridin-2-yl)-3-[(piperidin-4-ylmethyl)amino]pyridine-2-carboxamide (100 mg, 0.29 mmol) and cyclopentanone (122 mg, 1.45 mmol) yielded 70 mg (58%) of the title compound.

$^1$H-NMR, IR; IS-MS, m/e 414(m+1); Analysis for $C_{22}H_{28}ClN_5O \cdot 0.5\, H_2O$:

| | | | |
|---|---|---|---|
| Calcd: | C, 62.47; | H, 6.91; | N, 16.56; |
| Found: | C, 62.95; | H, 6.69; | N, 16.07. |

EXAMPLE 17

Preparation of N-(5-Chloropyridin-2-yl)-3-[(1-cyclohexylpiperidin-4-ylcarbonyl)amino]pyridine-2-carboxamide Hydrochloride

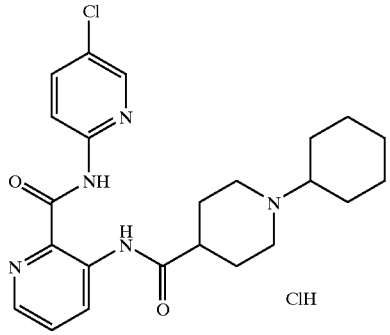

By methods substantially equivalent to those described in example 6-C, N-(5-chloropyridin-2-yl)-3-[(1-cyclohexylpiperidin-4-ylcarbonyl)amino]pyridine-2-carboxamide hydrochloride (0.183 g, 46%) was prepared from N-(5-chloropyridin-2-yl)-3-[(piperidin-4-ylcarbonyl)amino]pyridine-2-carboxamide trifluoroacetate and cyclohexanone. The compound was purified by preparative RPHPLC (C18), eluting with a linear gradient of 80/20 to 50/50 (0.01% HCl/acetonitrile) over 180 min.

$^1$H-NMR; IS-MS, m/e 442.2 (m+1); Analysis for $C_{23}H_{28}N_5O_2Cl \cdot 1.1HCl \cdot 1.0H_2O$:

| | | | | |
|---|---|---|---|---|
| Calcd: | C, 55.24; | H, 6.27; | N, 14.01; | Cl, 14.89; |
| Found: | C, 55.04; | H, 6.01; | N, 13.89; | Cl, 14.59. |

EXAMPLE 18

Preparation of N-(5-Chloropyridin-2-yl)-3-[[1-(4-pyridinyl)piperidin-4-ylmethyl]amino]pyridine-2-carboxamide

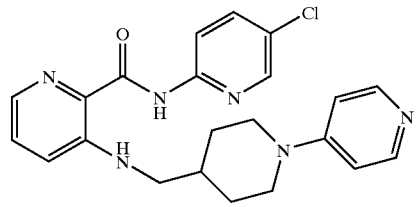

A pressure tube (Aldrich) was charged with N-(5-chloropyridin-2-yl)-3-[(piperidin-4-ylmethyl)amino]pyridine-2-carboxamide (500 mg, 1.45 mmol), 4-chloropyridine hydrochloride (435 mg, 2.90 mmol), triethylamine (293 mg, 2.90 mmol) and EtOH (5 mL), sealed, and placed in a 110° C. bath. After 16 h, the mixture was cooled, concentrated, and the residue purified by column chromatography (SiO$_2$: 5 to 7.5% methanol:methylene chloride) yielding 100 mg (16%) of the title compound.

$^1$H-NMR, IR; IS-MS, m/e 423 (m+1); Analysis for $C_{22}H_{23}ClN_6O$:

| | | | |
|---|---|---|---|
| Calcd: | C, 62.48; | H, 5.48; | N, 19.87; |
| Found: | C, 61.94; | H, 5.52; | N, 19.71. |

EXAMPLE 19

Preparation of N-(5-Chloropyridin-2-yl)-3-[(1-isoamylpiperidin-4-ylcarbonyl)amino]pyridine-2-carboxamide Hydrochloride

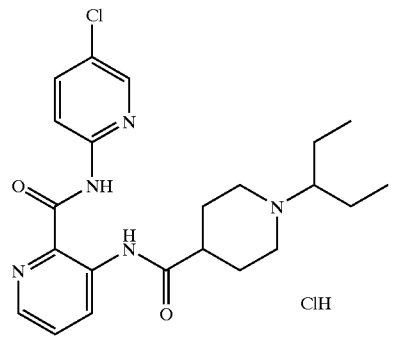

By methods substantially equivalent to those described in example 6-C, N-(5-chloropyridin-2-yl)-3-[(1-isoamylpiperidin-4-ylcarbonyl)amino]pyridine-2-carboxamide hydrochloride (0.083 g, 21%) was prepared from N-(5-chloropyridin-2-yl)-3-[(piperidin-4-ylcarbonyl)amino]pyridine-2-carboxamide trifluoroacetate and 3-pentanone. The compound was purified by preparative RPHPLC (C18), eluting with a linear gradient of 80/20 to 50/50 (0.01% HCl/acetonitrile) over 180 min.

$^1$H-NMR; IS-MS, m/e 430.4 (m+1); Analysis for $C_{22}H_{28}N_5O_2Cl \cdot 1.0HCl \cdot 0.2H_2O$:

| | | | | |
|---|---|---|---|---|
| Calcd: | C, 56.22; | H, 6.30; | N, 14.90; | Cl, 15.09; |
| Found: | C, 56.22; | H, 6.29; | N, 14.77; | Cl, 15.46. |

EXAMPLE 20

Preparation of 5-Chloro-N-(5-chloropyridin-2-yl)-2-[(1-isoprppylpiperidin-4-ylmethyl)amino]pyridine-3-carboxamide Dihydrochloride

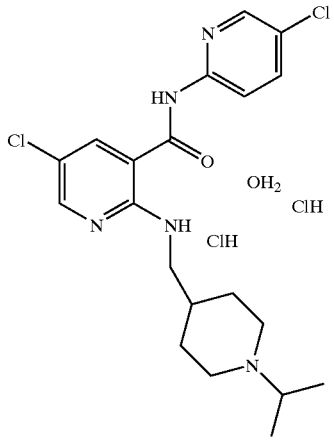

A. 1-Isopropylpiperidine-4-carboxamide.

A solution of 200 mL of DMF, containing 50.0 g of isonicotinamide and 60 mL of 2-bromopropane, was refluxed 5.75 h. A white insoluble solid filtered from this cool solution gave 64.9 g (65%) of 1-isopropylpyridinium-4-carboxamide bromide, m/e=165, NMR. Catalytic reduction of this salt, with $PtO_2$ in MeOH, gave 65.2 g (98%) of 1-isopropylpiperidine-4-carboxamide hydrobromide, m/e= 171. An aqueous solution of this salt was basified, evaporated to dryness, and extracted with EtOAc to give 39.7 g (90%) of 1-isopropylpiperidine-4-carboxamide free base.

B. 1-Isopropylpiperidine-4-methylamine.

To a suspension of 10.0 g of LAH, in 500 mL of dry THF, at room temperature, was added portionwise 39.7 g of 1-isopropylpiperidine-4-carboxamide, and the mixture was refluxed 18 h. The cooled reaction mixture was diluted with 150 mL THF and treated dropwise with 10 mL $H_2O$ and 10 mL 5 N NaOH, respectively. Gray mixture was refluxed 18 h, filtered and evaporated. Residue partially dissolved in hexane to give 25.5 g of crude yellow liquid and 6.9 g hexane insoluble starting carboxamide. HPLC purification of 25.5 g liquid with 20% MeOH-EtOAc/Silica Gel gave 1-isopropylpiperidine-4-methylamine (8.5 g, 28%).

NMR, m/e=157.

C. 5-Chloro-N-(5-chloropyridin-2-yl)-2-[(1-isopropylpiperidin-4-ylmethyl)amino]pyridine-3-carboxamide Hydrochloride.

A suspension of N-(5-chloropyridin-2-yl)-2,5-dichloropyridine-3-carboxamide 0.607 g, 2.05 mmol) and 1-isopropylpiperidine-4-methylamine (510 mg) in acetonitrile (5 mL) was heated in a sealed tube for 24 hours. Filtered the solids and purified by RPHPLC and the pure product containing fractions were combined and lyophilized to give 0.256 g of tan powder.

$^1$H-NMR; FD-MS, m/e 422.1 (m+1).

EXAMPLE 21

Preparation of 4-[(4-t-Butylbenzoyl)amino]-N-(5-chloropyridin-2-yl)pyridine-3-carboxamide

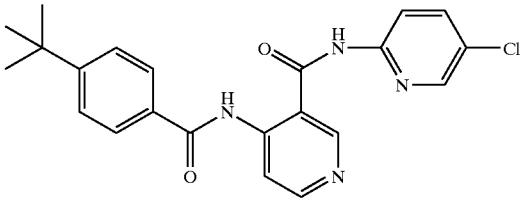

A. 4-(Boc-amino)pyridine.

To a stirring solution of 4-aminopyridine (15 g, 159 mmol) and triethylamine (24 mL, 175 mmol) in DMF (300 mL) was added di-t-butyl dicarbonate (38 g, 175 mmol). After stirring overnight, the solvent was removed in vacuo, the residue was dissolved in ethyl acetate (500 mL), and the solution was washed with satd aq sodium bicarbonate, water and then brine. The organic phase was then dried with $MgSO_4$, filtered and concentrated in vacuo to a volume of about 100 mL. The mixture was then sonicated and the precipitate was filtered and dried in vacuo to give 9.52 g (31%) of the title compound. To the mother liquor was added about 50 g of silica gel and the mixture was concentrated in vacuo. The resulting dry pack was loaded onto a silica gel column prepared with a solution of 50% ethyl acetate in hexanes and eluted with 20% ethyl acetate in dichloromethane, followed by a step gradient of 50% ethyl acetate in hexanes through ethyl acetate. The product containing fractions were combined and concentrated in vacuo to give another 16.16 g (52%) of the title compound.

$^1$H-NMR; IS-MS, m/e 195.3 (m+1).

B. 4-(Boc-amino)pyridine-3-carboxylic Acid.

To a stirring solution of 4-(Boc-amino)pyridine (1.027 g, 5.30 mmol) in THF at −36° C. (internal temperature) was added a 1.7 M solution of t-butyl lithium in pentane(6.5 mL, 11 mmol), and the rate of addition was controlled so as to keep the internal temperature below −28° C. After an additional hour (temperature kept between −30° C. and −50° C.) carbon dioxide (g) was bubbled through the solution and the cold bath was removed. After about 15 min, the mixture was poured into ice water and the aqueous phase was washed with dichloromethane. The pH was adjusted to 4–5 with citric acid and the resulting precipitate was washed with dichloromethane and methanol and dried in vacuo to give 0.811 g (64%) of an off-white solid.

$^1$H-NMR; IS-MS, m/e 239.0 (m+1); Analysis for $C_{11}H_{14}N_2O_4$:

| Calcd: | C, 55.46; | H, 5.92; | N, 11.76; |
|---|---|---|---|
| Found: | C, 55.73; | H, 6.07; | N, 11.75. |

C. Methyl 4-(Boc-amino)pyridine-3-carboxylate.

To a stirring suspension of 4-(Boc-amino)pyridine-3-carboxylic acid (1.04 g, 4.37 mmol) in methanol (3.5 mL) was added a 2 M solution of (trimethylsilyl)diazomethane in hexanes (3.5 mL, 7 mmol). After 15 min, acetic acid was added and the solvents were removed in vacuo. The residue was chromatographed over silica gel, eluting with a step gradient of 20% ethyl acetate in hexanes through 70% ethyl acetate in hexanes. The product containing fractions were combined and concentrated in vacuo to give 0.894 g (81%) of a white solid.
$^1$H-NMR.

D. Methyl 4-Aminopyridine-3-carboxylate.

Methyl 4-(Boc-amino)pyridine-3-carboxylate (2.38 g, 9.4 mmol) was dissolved in TFA (20 mL) and the solution was allowed to stir for 45 min. The solvent was removed in vacuo and the residue was partitioned between 25% isopropanol in chloroform and satd aq sodium bicarbonate. The layers were separated and the aqueous phase was extracted again with 25% isopropanol in chloroform. The combined organic extracts were dried (MgSO$_4$), filtered and concentrated in vacuo to give a solid which was washed with diisopropyl ether and dried in vacuo to give 1.327 g (92%) of an off-white solid.
$^1$H-NMR; IS-MS, m/e 153.1 (m+1); Analysis for C$_7$H$_8$N$_2$O$_2$:

| Calcd: | C, 55.26; | H, 5.30; | N, 18.41; |
|---|---|---|---|
| Found: | C, 55.31; | H, 5.36; | N, 18.42. |

E. Methyl 4-(4-t-Butylbenzoyl)aminopyridine-3-carboxylate.

To a stirring suspension of methyl 4-aminopyridine-3-carboxylate (0.161 g, 1.059 mmol), 4-dimethylaminopyridine (0.017 g, 0.138 mmol) and N,N-diisopropylethylamine (0.3 ML, 1.7 mmol) in dichloromethane (5 mL) was added 4-t-butylbenzoyl chloride (0.3 mL, 1.5 mmol). After 2 h, the mixture was diluted with ethyl acetate and satd aq sodium bicarbonate. The layers were separated and the organic phase was washed with satd aq sodium bicarbonate, then dried with MgSO$_4$, filtered and concentrated in vacuo. The residue was suspended in diisopropyl ether with vigorous stirring and the solid was filtered and dried in vacuo to give 0.257 g (78%) of a white solid.
$^1$H-NMR; IS-MS, m/e 313.0 (m+1); Analysis for C$_{18}$H$_{20}$N$_2$O$_3$:

| Calcd: | C, 69.21; | H, 6.45; | N, 8.97; |
|---|---|---|---|
| Found: | C, 69.43; | H, 6.37; | N, 9.15. |

F. 4-(4-t-Butylbenzoyl)aminopyridine-3-carboxylic Acid.

To a stirring solution of methyl 4-(4-t-butylbenzoyl) aminopyridine-3-carboxylate (0.156 g, 0.5 mmol) in THF (4 mL) and methanol (1 mL), was added a 1 M solution of aq LiOH (0.6 mL, 0.6 mmol). After 1 h, the solvent was removed in vacuo and the residue was partitioned between water and diethyl ether. The aqueous phase was separated and the pH was adjusted to 2–3 with citric acid. The precipitate was isolated by filtration and washed with water, with 25% isopropanol in chloroform and with diethyl ether and dried in vacuo to give 0.138 g (92%) of a white solid.
$^1$H-NMR; IS-MS, m/e 299.1 (m+1).

G. 2-(4-t-Butylphenyl)-4H-6-aza-3,1-benzoxazin-4-one.

To a stirring suspension of 4-(4-t-butylbenzoyl) aminopyridine-3-carboxylic acid (0.419 g, 1.4 mmol) in DMF (14 mL) was added 1-(3-dimethylaminopropyl)-3-ethylcarbodiimide hydrochloride (0.374 g, 1.96 mmol). After stirring overnight, the solvent was removed in vacuo and the residue was chromatographed over silica gel, eluting with a step gradient of 20% ethyl acetate in hexanes through 60% ethyl acetate in hexanes. The product containing fractions were combined and concentrated in vacuo to give 0.326 g (66%) of a white solid.
$^1$H-NMR; FD-MS, m/e 280 (m+1); Analysis for C$_{17}$H$_{16}$N$_2$O$_2$:

| Calcd: | C, 72.84; | H, 5.75; | N, 9.99; |
|---|---|---|---|
| Found: | C, 72.54; | H, 5.78; | N, 10.11. |

H. 4-[(4-t-Butylbenzoyl)amino]-N-(5-chloropyridin-2-yl)pyridine-3-carboxamide.

To a stirring solution of 2-amino-5-chloropyridine (0.11 g, 0.85 mmol) in THF (12 mL) at 0° C. was added a 1 M solution of allylmagnesium bromide in diethyl ether (0.83 mL, 0.83 mmol). After 20 min, 2-[4-t-butylphenyl]-4H-6-aza-3,1-benzoxazin-4-one (0.115 g, 0.41 mmol) was added and the cold bath was removed. After 2 h, the mixture was diluted with ethyl acetate and washed three times with brine. The organic phase was dried (MgSO$_4$), filtered and concentrated in vacuo. The solid was recrystallized from diethyl ether then washed several times with mixtures of ether/ hexanes and dried to give 0.138 g (82%) of pale yellow needles.
$^1$H-NMR; IS-MS, m/e 409.5 (m+1); Analysis for C$_{22}$H$_{21}$N$_4$O$_2$Cl:

| Calcd: | C, 64.62; | H, 5.18; | N, 13.70; |
|---|---|---|---|
| Found: | C, 64.65; | H, 5.18; | N, 13.95. |

EXAMPLE 22

Preparation of N-(5-Chloropyridin-2-yl)-4-[(1-isopropylpiperidin-4-ylcarbonyl)amino]pyridine-3-carboxamide Dihydrochloride

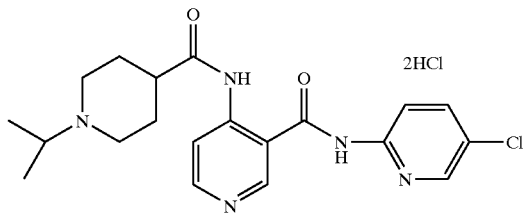

A. Methyl 4-[(1-Boc-piperidin-4-ylcarbonyl)amino]pyridine-3-carboxylate.

By methods substantially equivalent to those described in example 6-A, methyl 4-[(1-Boc-piperidin-4-ylcarbonyl) amino]pyridine-3-carboxylate (0.324 g, 84%) was prepared from methyl 1-Boc-piperidin-4-ylcarbonyl chloride and methyl 4-aminopyridine-3-carboxylate.
$^1$H-NMR; IS-MS, m/e 364.1 (m+1); Analysis for C$_{18}$H$_{25}$N$_3$O$_5$:

| Calcd: | C, 59.49; | H, 6.93; | N, 11.56; |
|---|---|---|---|
| Found: | C, 59.95; | H, 7.01; | N, 11.49. |

B. 4-[(1-Boc-piperidin-4-ylcarbonyl)amino]pyridine-3-carboxylic Acid.

By methods substantially equivalent to those described in example 21-F, 4-[(1-Boc-piperidin-4-ylcarbonyl)amino]- pyridine-3-carboxylic acid (0.148 g, 69%) was prepared from methyl 4-[(1-Boc-piperidin-4-ylcarbonyl)amino]pyridine-3-carboxylate.

¹H-NMR; IS-MS, m/e 350.4 (m+1).

C. N-(5-Chloropyridin-2-yl)-4-[(1-Boc-piperidin-4-ylcarbonyl)amino]pyridine-3-carboxamide.

By methods substantially equivalent to those described in example 21-G and 21-H, N-(5-chloropyridin-2-yl)-4-[(1-Boc-piperidin-4-ylcarbonyl)amino]pyridine-3-carboxamide (0.360 g, 50% for 2 steps) was prepared from 4-[(1-Boc-piperidin-4-ylcarbonyl)amino]pyridine-3-carboxylic acid and 5-chloro-2-aminopyridine.

¹H-NMR; IS-MS, m/e 460.4 (m+1); Analysis for $C_{22}H_{26}ClN_5O_4$:

| Calcd: | C, 57.45; | H, 5.70; | N, 15.23; | Cl, 7.71; |
| --- | --- | --- | --- | --- |
| Found: | C, 57.15; | H, 5.78; | N, 14.88; | Cl, 8.09. |

D. N-(5-Chloropyridin-2-yl)-4-[(piperidin-4-ylcarbonyl)amino]pyridine-3-carboxamide Trifluoroacetate.

By methods substantially equivalent to those described in example 6-B, N-(5-chloropyridin-2-yl) -4-[(piperidin-4-ylcarbonyl)amino]pyridine-3-carboxamide trifluoroacetate (53 mg, 71%) was prepared from N-(5-chloropyridin-2-yl)-4-[(1-Boc-piperidin-4-ylcarbonyl)amino]pyridine-3-carboxamide.

¹H-NMR; IS-MS, m/e 360.1 (m+1).

E. N-(5-Chloropyridin-2-yl) -4-[(1-isopropylpiperidin-4-ylcarbonyl)amino]pyridine-3-carboxamide Hydrochloride.

By methods substantially equivalent to those described in example 6-C, N-(5-chloropyridin-2-yl)-4-[(1-isopropylpiperidin-4-ylcarbonyl)amino]pyridine-3-carboxamide hydrochloride (0.219 g, 50%) was prepared from N-(5-chloropyridin-2-yl)-4-[(piperidin-4-ylcarbonyl)amino]pyridine-3-carboxamide trifluoroacetate and acetone. The compound was purified by preparative RPHPLC (C18), eluting with a linear gradient of 95/5 to 60/40 (0.01% HCl/acetonitrile) over 200 min.

¹H-NMR; FD-MS, m/e 402.3 (m+1); Analysis for $C_{20}H_{24}N_5O_2Cl.2.4HCl.3.6H_2O$:

| Calcd: | C, 43.34; | H, 6.11; | N, 12.64; | Cl, 21.75; |
| --- | --- | --- | --- | --- |
| Found: | C, 43.55; | H, 5.90; | N, 12.32; | Cl, 21.91. |

EXAMPLE 23

Preparation of N-(5-Chloropyridin-2-yl) -2-[(1-isopropylpiperidin-4-ylmethyl)amino]pyridine-3-carboxamide Trihydrochloride

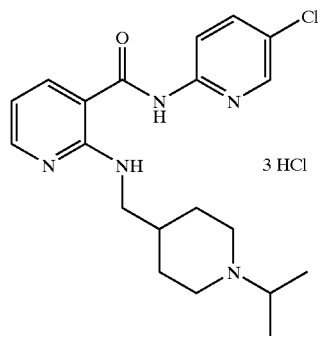

A. 2-Chloro-N-(5-chloropyridin-2-yl)nicotinamide.

By methods substantially equivalent to those described in example 14-A, 2-chloro-N-(5-chloropyridin-2-yl) nicotinamide was prepared from 2-amino-5-chloropyridine and 2-chloronicotinoyl chloride.

B. N-(5-Chloropyridin-2-yl)-2-[(1-isopropylpiperidin-4-ylmethyl)amino]pyridine-3-carboxamide Hydrochloride.

A solution of 0.57 g of 2-chloro-N-(5-chloropyridin-2-yl) nicotinamide, in 7 mL of pyridine, was treated with 0.64 g of 1-isopropylpiperidine-4-methylamine, and the mixture was refluxed 68 h. The mixture was cooled to room temperature and then treated with 1 mL of 5 N NaOH and evaporated to dryness. The EtOH extract was purified by radial chromatography (10% MeOH-CHCl₃, 1% NH₄OH) to give 0.25 g of free base. The HCl salt was isolated as an amorphous foam (0.21 g, 19%).

¹H-NMR; IS-MS, m/e 388 (m+1); Analysis for $C_{20}H_{26}ClN_5O.3HCl.1.75H_2O$:

| Calcd: | C, 45.42; | H, 6.19; | N, 13.24; |
| --- | --- | --- | --- |
| Found: | C, 45.64; | H, 5.97; | N, 12.85. |

EXAMPLE 24

Preparation of N-(5-Chloropyridin-2-yl)-3-[(1-isopropylpiperidin-4-ylcarbonyl)amino]-6-methylpyridine-2-carboxamide Hydrochloride

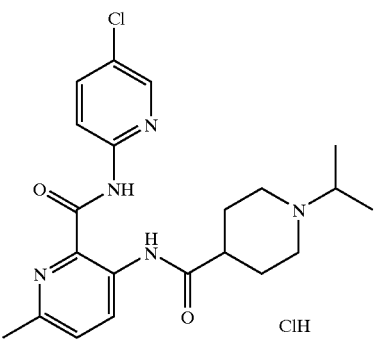

A. 3-Amino-N-(5-chloropyridin-2-yl)-6-methylpyridine-2-carboxamide.

Using methods substantially equivalent to those described in Example 2-A, 3-amino-N-(5-chloropyridin-2-yl)-6- methylpyridine-2-carboxamide (16 g, 46%) was prepared from 3-amino-2-chloro-6-methylpyridine and 2-amino-5-chloropyridine.

$^1$H NMR; FIA-MS, m/e 263.1 (m+1).

B. 3-[(1-tert-Butoxycarbonylpiperidin-4-ylcarbonyl)amino]-N-(5-chloropyridin-2-yl)-6-methylpyridine-2-carboxamide.

Using methods substantially equivalent to those described in Example 6-A, 3-[(1-tert-butoxycarbonylpiperidin-4-ylcarbonyl)amino]-N-(5-chloropyridin-2-yl)-6-methylpyridine-2-carboxamide (1.26 g, 93%) was prepared from 3-amino-N-(5-chloropyridin-2-yl)-6-methylpyridine-2-carboxamide (0.75 g, 2.85 mmol) and N-Boc-isonipecotic acid. The crude product was purified by chromatography over silica gel, eluting with a step gradient of 5–15% ethyl acetate in dichloromethane.

$^1$H NMR; IS-MS, m/e 474.1 (m+1), 472.3 (m−1); Analysis for $C_{23}H_{28}ClN_5O_4$:

| Calcd: | C, 58.29; | H, 5.95; | N, 14.78; |
|---|---|---|---|
| Found: | C, 58.01; | H, 5.90; | N, 14.90. |

C. N-(5-Chloropyridin-2-yl)-6-methyl-3-[(4-piperidinylcarbonyl)amino]pyridine-2-carboxamide Trifluoroacetate.

To a stirring solution of 3-[(1-tert-butoxycarbonylpiperidin-4-ylcarbonyl)amino]-N-(5-chloropyridin-2-yl)-6-methylpyridine-2-carboxamide (0.88 g, 1.86 mmol) and anisole (1.0 mL) in dichloromethane (40 mL) was added TFA (3.6 mL). After stirring for 4 h, the solvent was removed in vacuo and the residue was suspended in diethyl ether with vigorous stirring. After 30 min, the solid was filtered, washed several times with diethyl ether and then dried in vacuo to give (0.90 g, 99%) of a white solid.

$^1$H NMR; IS-MS, m/e 374.1 (m+1), 372.1 (m−1); Analysis for $C_{18}H_{20}ClN_5O_2 \cdot 1.2C_2HF_3O_2 \cdot 1.2H_2O$:

| Calcd: | C, 46.03; | H, 4.47; | N, 13.16; | F, 12.85; |
|---|---|---|---|---|
| Found: | C, 46.21; | H, 4.08; | N, 12.97; | F, 12.36. |

D. N-(5-Chloropyridin-2-yl)-3-[(1-isopropylpiperidin-4-ylcarbonyl)amino]-6-methylpyridine-2-carboxamide Hydrochloride.

To a stirring suspension of N-(5-chloropyridin-2-yl)-6-methyl-3-[ (4-piperidinylcarbonyl)amino]pyridine-2-carboxamide trifluoroacetate (0.75 g, 1.54 mmol) in methanol (11 mL) was added acetone (11 mL), followed by acetic acid (0.45 mL, 7.86 mmol), and then sodium cyanoborohydride (0.51 g, 7.7 mmol). After stirring overnight, the solution was treated with saturated aqueous ammonium chloride solution, concentrated, and partitioned between dichloromethane and saturated aqueous sodium bicarbonate. The organic phase was washed with brine, dried over magnesium sulfate, filtered, and concentrated. The crude product was purified by chromatography over silica gel, eluting with a step gradient of 0–10% 2 M solution of ammonia/methanol in dichloromethane. To a stirring solution of the purified product in dichloromethane was added 1.0 N hydrochloric acid in diethyl ether until precipitate formed. The mixture was filtered to give 0.28 g (40%) of a white solid.

$^1$H NMR; IS-MS, m/e 416.2 (m+1), 414.2 (m−1); Analysis for $C_{21}H_{26}ClN_5O_2 \cdot 1.8HCl \cdot 0.4H_2O$:

| Calcd: | C, 51.60; | H, 5.90; | N, 14.33; | Cl, 20.31; |
|---|---|---|---|---|
| Found: | C, 51.88; | H, 5.73; | N, 14.25; | Cl, 20.54. |

EXAMPLE 25

Preparation of N-(5-Chloropyridin-2-yl) -3-[1-isopropylpiperidin-4-ylmethyl)amino]pyrazine-2-carboxamide

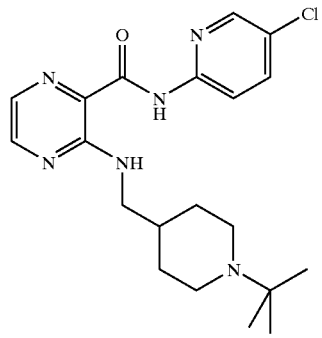

A. 2-Chloro-3-[(1-isopropylpiperidin-4-ylmethyl)amino]-pyrazine.

A mixture of of 2,3-dichloropyrazine (5.0 g, 32 mmol), 4-aminomethyl-1-isopropylpiperidine (5.3 g, 34 mmol), and pyridine (3 mL) in dry toluene (50 mL) was heated at 60° C. for 19 h. The cooled mixture was filtered and the filtrate was evaporated. This residue was refiltered from ether to give 6.0 g of crude product. Flash column purification with 10% MeOH-CHCl$_3$, 1% NH$_4$OH gave 2.9 g (33%) of the desired product B. N-(5-Chloropyridin-2-yl)-3-[(1-isopropylpiperidin-4-ylmethyl)amino]pyrazine-2-carboxamide.

A carbonylation mixture of 2-chloro-3-[(1-isopropylpiperidin-4-ylmethyl)amino]pyrazine (1.37 g, 5.10 mmol), 2-amino-5-chloropyridine (4.1 g, 3.19 mmol), 1,3-bis(di-phenylphosphino)propane (1.3 g, 3.15 mmol), palladium acetate (0.24 g, 1.1 mmol),and triethylamine (2.2 g, 21.7 mmol), in acetonitrile under a 54.4 bar carbon monoxide atmosphere was heated at 100° C. for 72 h. The reaction mixture was filtered and evaporated to give 6.74 g crude product. After basification with NaOH, extraction with ethyl acetate and evaporation of the organic phase, the residue was purified by flash-column chromatography over silica gel, eluting with 2.5% MeOH-CHCl$_3$, 0.25% NH$_4$OH, to give 1.43 g (72%) of the desired product.

$^1$NMR (300 MHz, CDCl$_3$) δ 10.40 (s, 1H); 8.59 (s, 1H); 8.28 (d, J=8.4 Hz, 1H); 8.30 (d, J=0.7 Hz, 1H); 8.23 (d, J=2.2 Hz, 1H) ; 7.74 (d, J=2.2 Hz, 1H); 7.70 (dd, J=6.2 Hz, 1H); 3.45 (dd, J=6.2 Hz, 2H); 2.96 (d, J=2.7 Hz, 2H); 2.78 (m, 1H); 2.20 (m, 2H); 1.88 (s, 1H); 1.84 (s, 1H); 1.66 (m, 1H); 1.45 (m, 2H); 1.08 (d. J=6.2 Hz, 6H). IS-MS, m/e=389.3 (m+1); Analysis for $C_{19}H_{25}ClN_6O \cdot 0.25\ H_2O$:

| Calcd: | C, 58.00; | H, 6.53; | N, 21.36; |
|---|---|---|---|
| Found: | C, 58.19; | H, 6.36; | N, 20.84. |

What is claimed is:

1. A compound of formula I

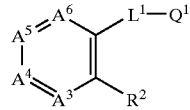

(or a pharmaceutically acceptable salt thereof) wherein;

$A^3, A^4, A^5$ and $A^6$, together with the two carbons to which they are attached, complete a substituted heteroaromatic ring in which
(a) one of $A^3, A^4, A^5$ and $A^6$ is N, and each of the others is $CR^3, CR^4, CR^5$ or $CR^6$, respectively; or
(b) $A^3$ and $A^6$ are each N, and $A^4$ and $A^5$ are $CR^4$ and $CR^5$, respectively; wherein
each of $R^3, R^4, R^5$ and $R^6$ is independently hydrogen or methyl, or one of $R^3, R^4, R^5$ and $R^6$ attached to a carbon which is not bonded to an N-atom is chloro and the others are hydrogen;

$L^1$ is —CO—NH— such that —$L^1$—$Q^1$ is —CO—NH—$Q^1$;

$Q^1$ is 2-pyridinyl (which bears a methyl, methoxy, methylthio, fluoro or chloro substituent at the 5-position), 3-pyridinyl (which bears a methyl, fluoro or chloro substituent at the 6-position), 2-pyrimidinyl (which may bear a methyl, fluoro or chloro substituent at the 5-position), 3-pyridazinyl (which may bear a methyl, fluoro or chloro substituent at the 6-position) or 2-benzothiazolyl (which may bear a methyl, fluoro, chloro-or bromo substituent at the 6-position);

$R^2$ is —$L^2$—$Q^2$ in which —$L^2$— is —NH—CO—, —NH—CO—X—, —NH—CO—O—X—, —NH—CO—NH—X— or —NH—CH$_2$—; and $Q^2$ is $Q^{2A}, Q^{2B}, Q^{2C}, Q^{2D}, Q^{2E}$ or $Q^{2F}$ wherein X is a single bond or methylene and the values of $L^2$ and $Q^2$ are together selected from —NH—CO—X—$Q^{2A}$, —NH—CO—O—X—$Q^{2A}$, —NH—CO—N—X—$Q^{2A}$, —NH—CH$_2$—$Q^{2A}$, —NH—CO—X—$Q^{2B}$, —NH—CO—$Q^{2C}$, —NH—CO—$Q^{2D}$, —NH—CO—$Q^{2E}$ and —NH—CO—$Q^{2F}$ in which:

$Q^{2A}$ (showing the $L^2$ to which it is attached) is

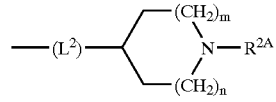

in which
each of m and n independently is 0 or 1, and
$R^{2A}$ is hydrogen, t-butyl, methylsulfonyl, —CHR$^y$R$^z$, —CHR$^w$R$^x$, or 4-pyridinyl (which is unsubstituted or bears a substituent R$^v$ at the 2- or 3-position) wherein R$^v$ is methyl, hydroxymethyl, {(1–2C)alkoxy}carbonyl; cyano, carbamoyl, thiocarbamoyl, or N-hydroxyamidino;
each of R$^w$ and R$^x$ independently is hydrogen or (1–3C)normal alkyl; or —CHR$^w$R$^x$ is 2-indanyl or (showing the nitrogen to which it is attached) is

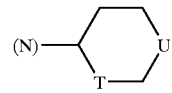

in which T is a single bond or methylene and U is methylene, ethylene, oxy, —S(O)$_q$— (wherein q is 0, 1 or 2) or imino (which may bear a methyl substituent), or T is ethan-1,1-diyl and U is a single bond or methylene;

R$^y$ is hydrogen or methyl; and

R$^z$ is isopropyl, t-butyl, (3–6C)cycloalkyl, phenyl (which is unsubstituted or bears one or more substituents independently selected from halo, methyl, methoxy and hydroxy), 4-quinolinyl or heteroaryl (which heteroaryl is a 5-membered aromatic ring which includes one to four heteroatoms selected from sulfur, oxygen and nitrogen or is a 6-membered aromatic ring which includes one to three nitrogen atoms, wherein the heteroaryl is attached at carbon and may bear one or more methyl substituents on carbon or nitrogen);

$Q^{2B}$ is 1-piperazinyl which bears at the 4-position the group $R^{2A}$ (defined as above);

$Q^{2C}$ is 3,4-didehydropiperidin-4-yl which bears at the 1-position the group $R^{2A}$ (defined as above);

$Q^{2D}$ is cyclohexyl which bears at the 4-position the group —NR$^s$R$^t$ in which each of R$^s$ and R$^t$ independently is hydrogen or methyl or R$^s$ and R$^t$ together are trimethylene or tetramethylene;

$Q^{2E}$ is 1-piperidinyl which bears at the 4-position the group —NR$^s$R$^t$ (defined as above); and $Q^{2F}$ (showing the $L^2$ to which it is attached) is

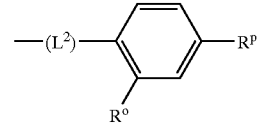

in which R$^o$ is hydrogen, halo, (1–6C)alkyl, hydroxy, (1–4C)alkoxy, benzyloxy or (1–4C)alkylthio; and R$^p$ is 1-hydroxyethyl, 1-hydroxy-1-methylethyl, 1-methoxy-1-methylethyl, 4-piperidinyl, 4-pyridinyl, dimethylaminosulfonyl or —J—R$^q$ in which J is a single bond, methylene, carbonyl, oxy, —S(O)$_q$— (wherein q is 0, 1 or 2), or —NR$^r$— (wherein R$^r$ is hydrogen or methyl); and R$^q$ is (1–6C)alkyl, phenyl, 3-pyridyl or 4-pyridyl.

2. The compound of claim 1 wherein halo is fluoro, chloro, bromo or iodo; (1–2C)alkyl is methyl or ethyl; (1–3C) normal alkyl is methyl, ethyl or propyl; (1–4C)alkyl is methyl, ethyl, propyl, isopropyl, butyl, isobutyl, or t-butyl; (1–6C)alkyl is methyl, ethyl, propyl, butyl, pentyl or hexyl; (3–6C)cycloalkyl is cyclopropyl, cyclobutyl, cyclopenytyl or cyclohexyl.

3. The compound of claim 2 wherein $Q^1$ is 5-chloropyridin-2-yl or 6-chloropyridazin-3-yl.

4. The compound of claim 3 wherein $R^2$ is (1-isopropylpiperidin-4-ylcarbonyl)amino, (1-cyclohexylpiperidin-4-ylcarbonyl)amino, [1-(tetrahydropyran-4-yl)-piperidin-4-ylcarbonyl]amino, or [1-(4-pyridinyl)piperidin-4-ylmethyl]amino.

5. The compound of claim 1 wherein $R^2$ is (1-isopropylpiperidin-4-ylcarbonyl)amino, (1-cyclohexylpiperidin-4-ylcarbonyl)amino, [1-(tetrahydropyran-4-yl)piperidin-4-ylcarbonyl]amino, or [1-(4-pyridinyl)piperidin-4-ylmethyl]amino.

6. The compound as claimed in any one of claims 1–5 and 4 wherein $A^3$ is N and each of $A^4$—$A^6$ is $CR^4$—$CR^6$ in which each of $R^4$—$R^6$ is hydrogen or $R^4$ and $R^6$ are each hydrogen and $R^5$ is chloro.

7. The compound as claimed in any one of claims 1–5 wherein $A^6$ is N and each of $A^3$—$A^5$ is $CR^3$—$CR^5$ in which each of $R^3$—$R^5$ is hydrogen or $R^3$ and $R^4$ are each hydrogen and $R^5$ is methyl.

8. The compound as claimed in any one of claims 1–5 or 7 wherein one of $A^3$, $A^4$, $A^5$ and $A^6$ is N, and each of the others is $CR^3$, $CR^4$, $CR^5$ or $CR^6$, respectively.

9. The compound as claimed in any one of claims 1–5 or 7 wherein $A^3$ and $A^6$ are each N, and $A^4$ and $A^5$ are $CR^4$ and $CR^5$, respectively.

10. The pharmaceutically acceptable salt of a compound of formula I as claimed in claim 1 which is an acid-addition salt made from a basic compound of formula I and an acid which provides a pharmaceutically acceptable anion or a salt which is made from an acidic compound of formula I and a base which provides a pharmaceutically acceptable cation.

11. A pharmaceutical formulation comprising in association with a pharmaceutically acceptable carrier, diluent or excipient, a novel compound of formula I (or a pharmaceutically acceptable salt thereof) as provided in claim 1.

12. A process for preparing a compound of formula I (or a pharmaceutically acceptable salt thereof) as provided in any of the above descriptions which is selected from (A) for a compound of formula I in which —$L^2$—$Q^2$, is —NH—CO—$Q^2$, —NH—CO—X—$Q^2$, —NH—CO—O—X—$Q^2$ or —NH—CO—NH—X—$Q^2$, acylating an amine of formula II,

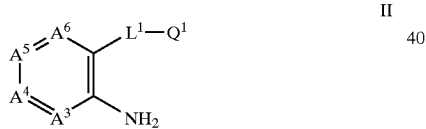

II using a corresponding acid of formula HO—CO—$Q^2$, HO—CO—X—$Q^2$, HO—CO—O—X—$Q^2$, or HO—CO—NH—X—$Q^2$, or an activated derivative thereof;

(B) for a compound of formula I in which —$L^2$—$Q^2$ is —NH—$CH_2$—$Q^2$, substituting the group $y^a$ of a compound of formula III

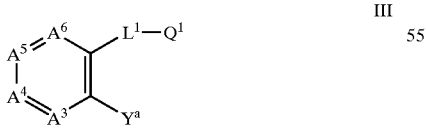

III in which $y^a$ is a conventional leaving group for nucleophilic aromatic substitution with an amine of formula $NH_2$—$CH_2$—$Q^2$;

(C) acylating an amine of formula $H_2N$—$Q^1$, or a deprotonated derivative thereof, using an acid of formula IV, or an activated derivative thereof;

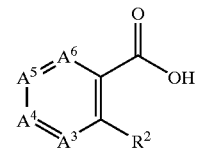

IV (D) for a compound of formula I in which $R^2$ is —NH—$CH_2$—$Q^{2A}$, alkylating an amine of formula II directly, using a compound of formula Y—$CH_2$—$Q^{2A}$, or indirectly by reductive alkylation using an aldehyde of formula $Q^{2A}$—CHO;

(E) for a compound of formula I in which $R^2$ is —NH—CO—O—X—$Q^{2A}$, or —NH—CO—NH—X—$Q^{2A}$, acylating an alcohol of formula HO—X—$Q^{2A}$ or an amine of formula $NH_2$—X—$Q^{2A}$, using an activated derivative of an acid of formula VI;

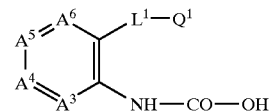

VI (F) for a compound of formula I in which $R^2$ is —NH—CO—X—$Q^{2B}$ in which X is a single bond, acylating at the 1-position a piperazine of formula H—$Q^{2B}$, using an activated derivative of an acid of formula VI;

(G) for a compound of formula I in which $R^2$ is —NH—CO—X—$Q^{2B}$ in which X is methylene, alkylating at the 1-position a piperazine of formula H—$Q^{2B}$, using an alkylating agent of formula VII

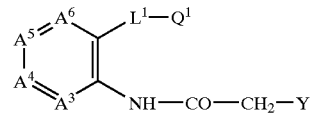

VII in which Y is a leaving group;

(H) for a compound of formula I in which $R^{2A}$ is methylsulfonyl, substituting the amino nitrogen of a corresponding compound of formula I in which $R^{2A}$ is hydrogen using an activated derivative of methanesulfonic acid;

(I) for a compound of formula I in which $R^{2A}$ is —$CHR^yR^z$ or —$CHR^wR^x$, alkylating the amino nitrogen of a corresponding compound of formula I in which $R^{2A}$ is hydrogen using an alkylating agent of formula Y—$CHR^yR^z$ or Y—$CHR^wR^x$ or reductively alkylating the amine using a compound of formula $R^y$—CO—$R^z$ or $R^w$—CO—$R^x$;

(J) for a compound of formula I in which $R^{2A}$ is 4-pyridinyl (which is unsubstituted or bears a substituent $R^v$ at the 2- or 3-position), substituting the amino nitrogen of a corresponding compound of formula I in which $R^{2A}$ is hydrogen using a corresponding pyridine reagent bearing a leaving group Y at the 4-position;

(K) for a compound of formula I in which $R^{2A}$ is 4-pyridinyl in which $R^v$ is alkoxycarbonyl, esterifying a corresponding compound of formula I in which $R^v$ is carboxy;

(L) for a compound of formula I in which $R^{2A}$ is 4-pyridinyl in which $R^v$ is hydroxymethyl, reducing the ester of a corresponding compound of formula I in which $R^v$ is alkoxycarbonyl;

(M) for a compound of formula I in which $R^{2A}$ is 4-pyridinyl in which $R^v$ is carbamoyl, amidating the ester of a corresponding compound of formula I in which $R^v$ is alkoxycarbonyl;

(N) for a compound of formula I in which $R^{2A}$ is 4-pyridinyl in which $R^v$ is thiocarbamoyl, adding $H_2S$ to the nitrile of a corresponding compound of formula I in which $R^v$ is cyano;

(O) for a compound of formula I in which $R^{2A}$ is 4-pyridinyl in which $R^v$ is N-hydroxyamidino, adding $H_2NOH$ to the nitrile of a corresponding compound of formula I in which $R^v$ is cyano;

(P) for a compound of formula I in which $R^{2A}$ is 4-pyridinyl in which $R^v$ is carboxy, decomposing the ester of a corresponding compound of formula I in which $R^v$ is alkoxycarbonyl;

(Q) for a compound of formula I in which —$NR^sR^t$ is other than amino, alkylating a corresponding compound of formula I in which —$NR^sR^t$ is amino using a conventional method;

(R) for a compound of formula I which bears —$NR^sR^t$, reductively alkylating H—$NR^sR^t$ using a corresponding compound but in which the carbon to bear the —$NR^sR^t$ group bears an oxo group;

(S) for a compound of formula I in which $R^p$ is 1-hydroxy-1-methylethyl, adding a methyl group to the carbonyl group of a corresponding compound of formula I in which $R^p$ is acetyl using an organometallic reagent;

(T) for a compound of formula I in which $R^p$ is 1-methoxy-1-methylethyl, treating a corresponding compound of formula I in which $R^p$ is 1-hydroxy-1-methylethyl with methanol and an acid catalyst;

whereafter, for any of the above procedures, when a functional group is protected using a protecting group, removing the protecting group;

whereafter, for any of the above procedures, when a pharmaceutically acceptable salt of a compound of formula I is required, it is obtained by reacting the basic form of a basic compound of formula I with an acid affording a physiologically acceptable counterion or the acidic form of an acidic compound of formula I with a base affording a physiologically acceptable counterion or by any other conventional procedure;

and wherein, unless otherwise specified, $A^3$—$A^6$, $L^1$, $Q^1$ and $R^2$ have any of the values defined in claim 1.

13. A method of inhibiting factor Xa comprising administering to a mammal in need of treatment, a compound of formula I as provided in claim 1.

* * * * *